United States Patent [19]
Xu et al.

[11] Patent Number: 5,916,919
[45] Date of Patent: Jun. 29, 1999

[54] RETROVIRUS PROTEASE INHIBITORS

[75] Inventors: Hong-Xi Xu, Halifax, Canada; Keng-Yeow Sim, Singapore, Singapore; Fa-Quan Zeng, Toronto, Canada; Min Wan, Houston, Tex.

[73] Assignees: Dalhousie University, Halifax, Canada; National University of Singapore, Singapore, Singapore

[21] Appl. No.: 08/884,663

[22] Filed: Jun. 27, 1997

[51] Int. Cl.[6] .......................... A61K 31/19; C07C 62/32; C07C 62/38
[52] U.S. Cl. ...................... 514/557; 562/508; 562/510
[58] Field of Search ................ 514/766, 33; 562/508; 568/832

[56] References Cited

U.S. PATENT DOCUMENTS

| | | | |
|---|---|---|---|
| 4,933,169 | 6/1990 | Shanbrom | 424/46 |
| 5,086,076 | 2/1992 | Herman | 514/724 |
| 5,204,324 | 4/1993 | Shanbrom | 514/2 |
| 5,411,733 | 5/1995 | Hozumi et al. | 424/195.1 |
| 5,527,890 | 6/1996 | Rao et al. | 536/5 |

OTHER PUBLICATIONS

Serra et al. Pharmacol. Res., 29(4), 359–66 (abstract), 1994.
Konoshima et al., J. Nat. Products, 50(6), 1167–70 (abstract), 1987.
Quere et al., Biochem. Biophys. Res. Commun., 227(2), 484–488, 1996.
Ryu et al., Arch. Pharmacol. Res., 16(4), 339–42 (abstract), 1993.
Brinkworth et al., *Biochem. Biophys. Res. Commun.*, 188: 631–637, 1992.
De–Tommasi, J. Nat. Prod., (Abstract), 55(8):1067–1073, 1992.
Fujioka, T., et al., *J. Nat. Prod.*, 57:243–247, 1994.
Hasegawa et al., Planta. Med., (Abstract), 60(3):240–243, 1994.
Hu, C. Q. et al., *J. Nat. Prod.*, 57:42–51, 1994.
Ito, M. et al., N., *Antiviral Res.*, 7: 127–137, 1987.
Kashiwada et al., *J. Med. Chem.*, 39(5):1016–1017, 1996.
Konoshima et al., J. Nat. Prod., (Abstract) 58(9):1372–1377, 1995.
Li et al., J. Nat. Prod. (Abstract), 56(7):1130–1133, 1993.
McQuade, T.J., et al., *Science*, 247:454–456, 1990.
Mirmala, M., NUS term finds possible link to AIDS cure, "New Straits Time", Jun. 25, 1996.
Pengsuparp et al., J. Nat. Prod. (Abstract), 58(7):1024–1031, 1995.
Piacente, S. et al., *J. Nat. Prod.*, 59:565–569, 1996.
Seelmeier, S. et al., *Proc. Natl. Acad. Sci. USA*, 85:6612–6616, 1988.
Shigenaga, S., et al., *Phytochemistry*, 24:115–118, 1985.
Soler et al., J. Med. Chem, 39(5):1069–1083, 1996.
Wang, S.N. et al., *J. Med. Chem.* 39: 2047–, 1996.
Xu, H. X., et al., *Heterocycles*, 38: 167–175, 1994.
Xu, H.X. et al., *Phyto. Res.*, 10:207–210, 1996.
Xu, H.X. et al., *J. Nat. Prod.* 59(7):643–645, 1996.
Yoshida, T., et al., *Chem. Pharm. Bull.*, 30:4245–4248, 1982.
Yoshida, T., et al., *Phytochemistry*, 24:1041–1046, 1985.
Yu et al., Chung. Kuo. Yao. Li. Hsueh. Pao. (Abstract), 15(2):103–106, 1994.

*Primary Examiner*—Phyllis G. Spivack
*Attorney, Agent, or Firm*—Bereskin & Parr; Micheline Gravelle

[57] ABSTRACT

A compound composition and method of treating a retrovirus infection are disclosed. In particular, isolated triterpenes have been shown to have significant inhibitory activity against HIV-1.

6 Claims, 14 Drawing Sheets

FORMULA I

RETROVIRUS PROTEASE INHIBITORS

FIELD OF THE INVENTION

The invention relates to triterpenes that are protease inhibitors and are useful in treating retroviral infections such as HIV and HTLV.

BACKGROUND OF THE INVENTION

Retroviruses are a family of viruses that contain an RNA genome and reverse transcriptase activity. Many classes of retroviruses have been identified, one of the major classes being the T-lymphotropic viruses which include HTLV-I which appears to be causative of adult T-cell leukemia-lymphoma; HTLV-II which appears to be related to a variant of hairy cell leukemia; and HIV-1 (HTLV-III) and HIV-2 which are linked to Acquired Immune Deficiency Syndrome (AIDS). Patients that test positive for HIV may be initially asymptomatic but typically develop AIDS related complex (ARC) followed by AIDS. The AIDS virus attacks and depletes the T lymphocytes causing severe immunosuppression in infected individuals which predisposes them to debilitating and ultimately fatal opportunistic infections.

No treatment is currently available to prevent or reverse the immunodeficiency of AIDS and ARC caused by the HIV virus. However, a number of compounds that interfere with viral replication have been developed to treat AIDS, including inhibitors of HIV reverse transcriptase (RT), such as nucleoside analogs including 3'-azido-3'-deoxythymidine (AZT, zidovidine) and 2',3'-dideoxy nucleosides such as 2', 3'-dideoxyinosine (DDI, ddI) and 2',3'-dideoxycytidine (DDC, ddC).

AZT is in use for early treatment of HIV positive individuals as well as individuals with ARC and AIDS. Unfortunately, AZT is frequently toxic, causing bone marrow suppression resulting in anemia leucopenia and thrombocytopenia. Also, AZT-resistant HIV strains have been observed after six months of AZT treatment. DDI and DDC have been approved for treatment of individuals with ARC and AIDS only in combination with AZT.

Consequently, the search for effective and non-toxic treatments for AIDS continues. Due to the toxicity associated with synthetic compounds, some groups are looking to natural sources in the search for a treatment for AIDS.

Some natural compounds have been reported to show anti-HIV activity. One compound is glycyrrhizin which is isolated from the aqueous extract of licorice root (*Glycyrrhiza radix*)[1], and is known as an anti-inflammatory substance in Chinese medicine. This compound consists of one molecule of glycyrrhetinic acid and two molecules of glucuronic acid. Ito et al [1] investigated its antiviral action on the human immunodeficiency virus in vitro, using cytopathic effect and plaque forming assay system in MT-4 cells. Cloned Molt-4 cells, which are sensitive to HIV and fused to giant cells after infection, were used as a parameter for cytopathic effect of HIV, Glycyrrhizin inhibited HIV-induced plaque formation in MT-4 cells at a concentration of 0.6 mM, the 50% inhibitory dose being 0.15 mM. Glycyrrhizin inhibited the cytopathic effect of HIV and HIV-specific antigen expression in MT-4 cells at a concentration of 0.3 and 0.6 mM, respectively. Furthermore, glycyrrhizin inhibited giant cell formation of HIV-infected Molt-4 clone No. 8 cells.

Wang et al [2] have reported that fifteen novel non-peptide HIV-1 protease inhibitors were identified by flexible 3D database pharmacophore searching of NCI DIS 3D database. The pharmacophores they used in the search were derived directly from the X-ray determined structure of protease-inhibitor complexes. These 15 inhibitors, belonging to nine different chemical classes, are promising leads for further development. The two best inhibitors found, the 4-hydroxycoumarin dimer and the 2-hydroxynapthoquinone tetramer, had $ID_{50}$ values of 0.32 and 0.75 $\mu$M, respectively, for HIV-1 protease inhibition.

*Ardisia japonica* (Thunb.) B1. (Myrsinaceae), in the form of a decoction of the roots, is widely used in traditional Chinese medicine to stop cough and uterine bleeding. In vitro anti-HIV activity studies, norbergenin and bergenin were found with moderate anti-HIV activity [3]. The most active compound was norgergenin, which exhibited an $EC_{50}$ value of 20 ($\mu$g/ml) and a $IC_{50}$ value of over 500 ($\mu$g/ml) with a selectivity index above 25.

From *Chrysanthemum morifolium* Ramar (Compositae), acacetin-7-O-$\beta$-D-galactopyranoside [4] was found to show significant anti-HIV activity. It has $IC_{50}$ 37 $\mu$M, $EC_{50}$ 8 $\mu$M and therapeutic index 5. Fujioka et al [5] found the MeOH extract of the leaves of *Syzigium claviflorum* (Roxb.) WALL (Myrtaceae) to show significant anti-HIV activity. Subsequent bioactivity-directed fractionation has resulted in the isolation of betulinic acid, platanic acid and dihydrobetulinic acid. These compounds were also potent inhibitors of HIV replication.

Geum is a genus of 65 species of rhizomatous herbs and subshrubs with simple or pinnately lobed leaves and regular flowers such as *G. borisii, G. chiloense, G. coccineum, G. macrophyllum, G. montanum, G. reptans, G. rivale, G. triflorum, G. urbanum* and *G. japonicum* etc.

*Geum japonicum* Thunb. is a perennial herb and the flowering plant of the Rosaceae family. The whole plant of *Geum japonicum* Thunb. has been used as a diuretic in traditional Chinese medicine [6]. The plants of Geum species are known to be rich in tannins. Several hydrolyzable tannins such as gemin A, gemin B, gemin C, gemin D, gemin E and gemin F have been isolated from *Geum japonicum* [7,8]. In the continuing investigation of the plant, some triterpenoids including 2-hydroxyoleanolic acid, 2-hydroxyursolic acid, 2,19-dihydroxy-ursolic acid, 2,3,19, 23-tetrahydroxyurs-12-en-28-oic acid 28-O-D-glucopyranoside were isolated by Shigenaga et al [9]. Xu et al [10] isolated geponin, 1,2,3-tri-O-galloyl-D-glucopyranside, blumenol A, gallic aldehyde, 3,4-dihydroxybenzoic acid, caffeic acid and kampferol-3-O-glucopyranside from *G. japonicum* aqueous extract. Of these isolated compounds, geponin and gallic aldehyde showed strong anti-HSV activity.

One potential target for inhibiting the HIV virus is to inhibit the aspartyl protease that is encoded for by HIV(HIV PR). The function of the HIV PR is essential for proper virion assembly and maturation. Inactivation of HIV PR by either mutation or chemical inhibition leads to the production of immature, non-infectious viral particles [11,12]. HIV PR inhibitors represent a new class of therapeutic agents that complements existing approaches to antiviral therapy that targets another enzyme, the HIV reverse transcriptase, as discussed above.

To date, most inhibitors of the HIV aspartic acid protease have been transition state mimetics. These have included reduced amides (Moore et al., Biochem. Biophys. Res. Commun. 159:420–425 (1989); Dreyer et al., Proc. Natl. Acad. Sci. 86:9752–9756 (1989)), hydroxyethylene isoteres (Dreyer et al., Proc. Natl. Acad. Sci. 86:9752–9756 (1989); Vacca et al., J. Med. Chem. 34:1225–1228 (1991); Tomasselli et al., J. Biol. Chem. 265:14675–14683 (1990); Roberts et al., Science 248:358–361 (1990)), statine analogs (Dryer et al., 1989), phosphinic acid derivatives (Grobelny et al., Biochem. Biophys, Res. Commun. 169:1111–1116 (1990)) and difluoroketone derivatives (Dreyer et al., 1989; Sham et al., Biochem Biophys. Res. Commun. 175:914–916 (1991)).

Some natural compounds have been reported to be inhibitory to HIV-1 protease [13]. Thus, traditional medicines utilizing natural products appear to be useful sources for discovery of new anti-AIDS agents.

SUMMARY OF THE INVENTION

The present inventors have isolated several triterpenes from natural sources which inhibit a retroviral protease, such as HIV protease.

In one aspect, the present invention relates to an isolated triterpene that can inhibit a retroviral protease. Preferably, the triterpene is of the Formula I shown in FIG. 11 where $R_1$ and $R_2$ are identical or different and are independently selected from H, OH, =O, $C_1$–$C_{10}$ unbranched alkoxy group, $C_1$–$C_{10}$ branched alkoxy group, $C_1$–$C_{10}$ unbranched acyloxyl group and $C_1$–$C_{10}$ branched acyloxy group; $R_3$, $R_4$, $R_5$ and $R_8$ are identical or different and are independently selected from H, C1–C10 branched alkyl group, $C_1$–$C_{10}$ unbranched alkyl group, $C_1$–$C_{10}$ branched alkoxy group, $C_1$–$C_{10}$ unbranched alkoxy group, a $C_1$–$C_{10}$ branched acyloxy group, a $C_1$–$C_{10}$ unbranched acyloxy group and a =O group; $R_6$, $R_7$ and $R_9$ are identical or different and are independently selected from a COOH group, a —COOCH$_3$ group, a —CH$_2$OH group and a $C_1$–$C_{10}$ unbranched alkyl group. Also included are pharmaceutically acceptable salts and modified derivatives of the compounds of Formula I such as the 28-beta-D-glucoside derivatives.

The triterpene may be isolated from a variety of plants including *Geum jeponicum, Anemarrhena asphodeloides, Brainia insignis, Epimedium sagittatum, Magnolia fargesii, Oldenlandia diffusa, Phellodendron amurense, Platycodon grandiflorum, Prunus mume, Punica granatum, Rhus javanica, Scutellaria buiculensis, Sophora japonica, Taraxacum mongolicum, Terminalia arjuna, Terminalia chebula, Woodfordia floribunda, Woodwardia orientalis.*

Anti-retroviral activity has been demonstrated in a methanol extract of *Geum jeponicum*. The present inventors have characterized the methanol abstract and have isolated nine triterpenes from the methanol extract and have determined that some of these have anti-HIV activity. The nine compounds are:

(1) 2-alpha, 19-alpha-dihydroxy-3-oxo-12-ursen-28-oic acid
(2) ursolic acid
(3) epimolic acid
(4) maslinic acid
(5) euscaphic acid
(6) tormentic acid
(7) 19-alpha-hydroxyasiatic acid
(8) 28-beta-D-glucoside of tormentic acid
(9) 28-beta-D-glucoside-19-alpha-hydroxyasiatic acid.

Consequently, the present invention provides a composition for treating a retroviral infection comprising at least one triterpene selected from the group consisting of (1) 2-alpha, 19-alpha-dihydroxy-3-oxo-12-ursen-28-oic acid (2) ursolic acid; (3) epimolic acid; (4) maslinic acid; (5) euscaphic acid; (6) tormentic acid; (7) 10-alpha-hydroxyasiatic acid; (8) 28-beta-D-glucoside of tormentic acid; and (9) 28-beta-D-glucoside-19-alpha-hydroxyasiatic acid or a pharmaceutically acceptable salt thereof, in admixture with a physiologically acceptable diluent or carrier. The composition can also include other agents that are useful in the treatment of retrovirus infections such as other HIV protease inhibitors as well as reverse transcriptase inhibitors. In a preferred embodiment the composition includes the triterpene 2-alpha, 19-alpha-dihydroxy-3-oxo-12-ursen-28-oic acid.

The present invention also includes a method for treating a retroviral infection comprising administering a therapeutically effective amount of an isolated triterpene to a mammal in need of such a treatment. The triterpene is preferably of the Formula I shown in FIG. 11 as defined above.

In one embodiment, the present invention provides a method of treating a retroviral infection comprising administering a therapeutically effective amount of at least one triterpene selected from the group consisting of (1) 2-alpha, 19-alpha-dihydroxy-3-oxo-12-ursen-28-oic acid; (2)ursolic acid; (3) epimolic acid; (4) maslinic acid; (5) euscaphic acid; (6) tormentic acid; (7) 19-alpha-hydroxyasiatic acid; (8) 28-beta-D-glucoside of tormentic acid; and (9) 28-beta-D-glucoside-19-alpha-hydroxyasiatic acid to a mammal in need of such a treatment.

In a preferred embodiment, the retroviral infection is Human Immunodeficiency Virus (HIV).

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

As hereinbefore mentioned, the present invention relates to isolated triterpenes that are useful in treating infections caused by a retrovirus such as Human Immunodeficiency Virus (HIV) or human T-cell leukemia virus (HTLV). The triterpenes act by inhibiting the protease activity of the retrovirus.

Broadly stated, the present invention relates to a composition for treating a retroviral infection comprising an isolated triterpene in admixture with a physiologically acceptable carrier or diluent.

Figure 11:
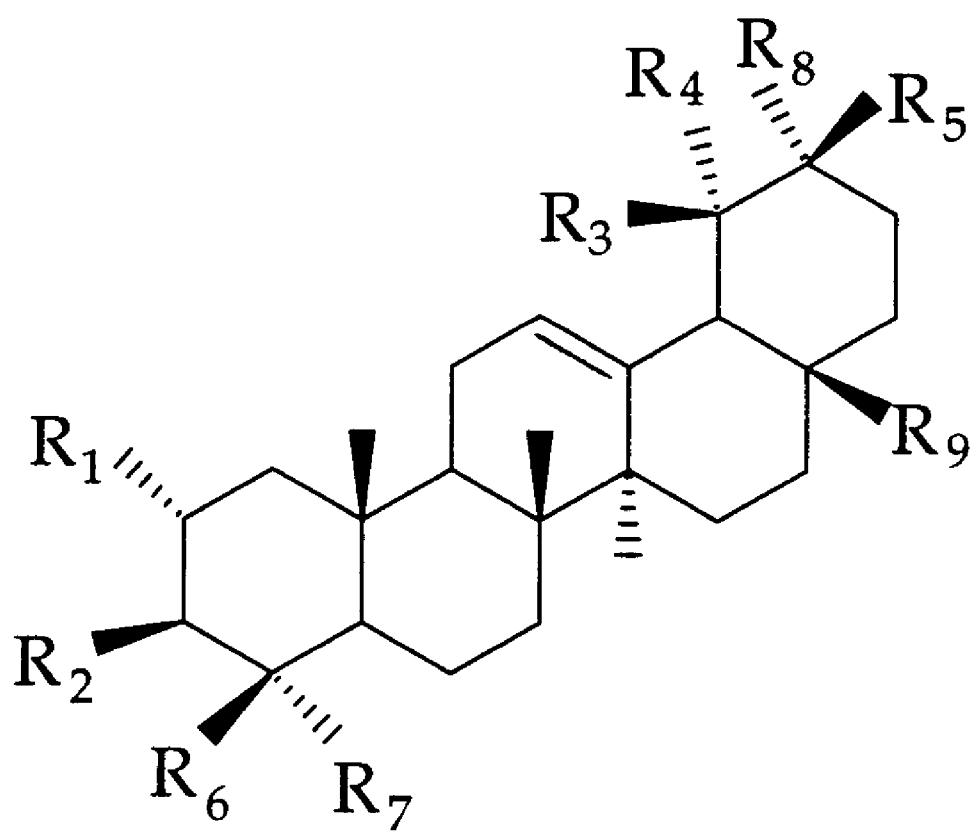
FIG. 11 shows a general chemical formula of a triterpene of the invention.

Preferably, the triterpene is of the Formula I shown in FIG. 11 wherein $R_1$ and $R_2$ are identical or different and are independently selected from H, OH, =O, $C_1$–$C_{10}$ unbranched alkoxy group, $C_1$–$C_{10}$ branched alkoxy group, $C_1$–$C_{10}$ unbranched acyloxyl group and $C_1$–$C_{10}$ branched acyloxy group; $R_3$, $R_4$, $R_5$ and $R_8$ are identical or different and are independently selected from H, $C_1$–$C_{10}$ branched alkyl group, $C_1$–$C_{10}$ unbranched alkyl group, $C_1$–$C_{10}$ branched acyloxy group, a $C_1$–$C_{10}$ unbranched acyloxy group, a $C_1$–$C_{10}$ branched acyloxy group, a $C_1$–$C_{10}$ unbranched acyloxy group and a =O group; $R_6$, $R_7$ and $R_9$ are identical or different and are independently selected from a COOH group, a —COOCH$_3$ group, a —CH$_2$OH group and a $C_1$–$C_{10}$ unbranched alkyl group.

The triterpene may be isolated from a variety of plants including *Geum jeponicum, Anemarrhena asphodeloides, Brainia insignis, Epimedium sagittatum, Magnolia fargesii, Oldenlandia diffusa, Phellodendron amurense, Platycodon grandiflorum, Prunus mume, Punica granatum, Rhus javanica, Scutellaria baicalensis, Sophora japonica, Taraxacum mongolicum, Terminalia arjuna, Terminalia chebula, Woodfordia floribunda, Woodwardia orientalis*.

In one embodiment, triterpenes isolated from the methanol extract of the whole plant of *Geum japonicum* were found to show significant inhibitory activity against HIV-1 protease. The triterpenes that have been isolated from the methanol extract are as follows:

(1) 2-alpha, 19-alpha-dihydroxy-3-oxo-12-ursen-28-oic acid (2) ursolic acid (3) 3-alpha-19-dihydroxy-12-ursen-28-oic acid or epimolic acid (4) maslinic acid (5) 2-alpha-3-alpha-19-alpha-trihydroxy-12-ursen-28-oic acid or euscaphic acid (6) 2-alpha-3-beta-19-alpha-trihydroxy-12-ursen-28-oic or tormentic acid (7) 2-alpha-3-beta-19alpha-23-tetrahydroxy-12-ursen-28-oic acid or 19-alpha-hydroxyasiatic acid (8) 28-beta-D-glucoside of tormentic acid (9) 28-beta-D-glucoside-19-alpha-hydroxyasiatic acid.

For ease of referral, the compounds have been given the following abbreviations and the terms may be used interchangeably throughout the application:

"2-alpha, 19-alpha-dihydroxy-3-oxo-12-ursen-28-oic acid" is also referred to as compound 1.

"ursolic acid" is also referred to as compound 2.

"3-alpha-19-dihydroxy-12-ursen-28-oic acid" is also "epimolic acid" and these are also referred to as compound 3.

"maslinic acid" is also referred to as compound 4.

"2-alpha-3-alpha-19-alpha-trihydroxy-12-ursen-28-oic acid" is also "euscaphic acid" and these are also referred to as compound 5.

"2-alpha-3-beta-19-alpha-trihydroxy-12-ursen-28-oic" is also "tormentic acid" and these are also referred to as compound 6.

"2-alpha-3-beta-19-alpha-23-tetrahydroxy-12-ursen-28-oic acid" is also "19-alpha-hydroxyasiatic acid" and these are also referred to as compound 7.

"28-beta-D-glucoside of tormentic acid" is also "28-beta-D-glucoside of 2-alpha-3-beta-19-alpha-trihydroxy-12-ursen-28-oic" and these are also referred to as compound 8.

"28-beta-D-glucoside-19-alpha-hydroxyasiatic acid" is also referred to as compound 9.

In one aspect, the present invention provides a composition for treating a retroviral infection comprising at least one isolated triterpene selected from the group consisting of (1) 2-alpha, 19-alpha-dihydroxy-3-oxo-12-ursen-28-oic acid; (2) ursolic acid; (3) epimolic acid; (4) maslinic acid; (5) euscaphic acid; (6) tormentic acid; and (7) 10-alpha-hydroxyasiatic acid; (8) 28-beta-D-glucoside of tormentic acid; and (9) 28-beta-D-glucoside-19-alpha-hydroxyasiatic acid; or a pharmaceutically acceptable salt thereof, in admixture with a physiologically acceptable diluent or carrier.

The term "pharmaceutically acceptable salt" as used herein means an organic or inorganic salt of a triterpene of the present invention that is suitable for administration to a mammal such as a human.

The term "physiologically acceptable diluent or carrier" means vehicles that are suitable for administration to a mammal, such as a human. Suitable diluents or carriers include sterile solutions such as saline, aqueous buffer solutions, glycerol, etc.

In a preferred embodiment, the composition comprises at least one triterpene selected from the group consisting of (1) 2-alpha, 19-alpha-dihydroxy-3-oxo-12-ursen-28-oic acid; (2) ursolic acid; and (4) maslinic acid or a pharmaceutically acceptable salt thereof. In a more preferred embodiment, the composition comprises (1) 2-alpha, 19-alpha-dihydroxy-3-oxo-12-ursen-28-oic acid or a pharmaceutically acceptable salt thereof.

In another aspect, the present invention provides a method of treating a retroviral infection comprising administering a therapeutically effective amount of at least one triterpene selected from the group consisting of (1) 2-alpha, 19-alpha-dihydroxy-3-oxo-12-ursen-28-oic acid; (2) ursolic acid; (3) epimolic acid; (4) maslinic acid; (5) euscaphic acid; (6) tormentic acid; (7) 19-alpha-hydroxyasiatic acid; (8) 28-beta-D-glucoside of tormentic acid; and (9) 28-beta-D-glucoside-19-alpha-hydroxyasiatic acid or a pharmaceutically acceptable salt thereof to a mammal in need of such a treatment.

In a preferred embodiment, the method comprises administering a therapeutically effective amount of at least one triterpene selected from the group consisting of (1) 2-alpha, 19-alpha-dihydroxy-3-oxo-12-ursen-28-oic acid; (2)ursolic acid; and (4) maslinic acid or a pharmaceutically acceptable salt thereof. The retroviral infection to be treated is preferably HIV.

Administration of a "therapeutically effective amount" of the compositions of the present invention is defined as an amount effective, at dosages and for periods of time necessary to achieve the desired result. The therapeutically effective amount of a triterpene of the invention may vary according to factors such as the disease state, age, sex, and weight of the individual. Dosage regima may be adjusted to provide the optimum therapeutic response. For example, several divided doses may be administered daily or the dose may be proportionally reduced as indicated by the exigencies of the therapeutic situation.

The composition may be administered in a convenient manner such as by injection (subcutaneous, intravenous, etc.), oral administration, inhalation, transdermal application or rectal administration. Depending on the route of administration, the triterpene may be coated in a material to protect the compound from the action of enzymes, acids and other natural conditions which may inactivate the compound.

A composition of the present invention can be administered to a subject in an appropriate carrier or diluent, or in an appropriate carrier such as liposomes. Liposomes include water-in-oil-in-water emulsions as well as conventional liposomes (Strejan et al., (1984) J. Neuroimmunol 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The physiologically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the triterpenes in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

When the active compound is suitably protected, as described above, the composition may be orally administered, for example, with an inert diluent or an assimilable edible carrier.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

The following non-limiting examples are illustrative of the present invention:

EXAMPLES

Example 1

Figure 12:
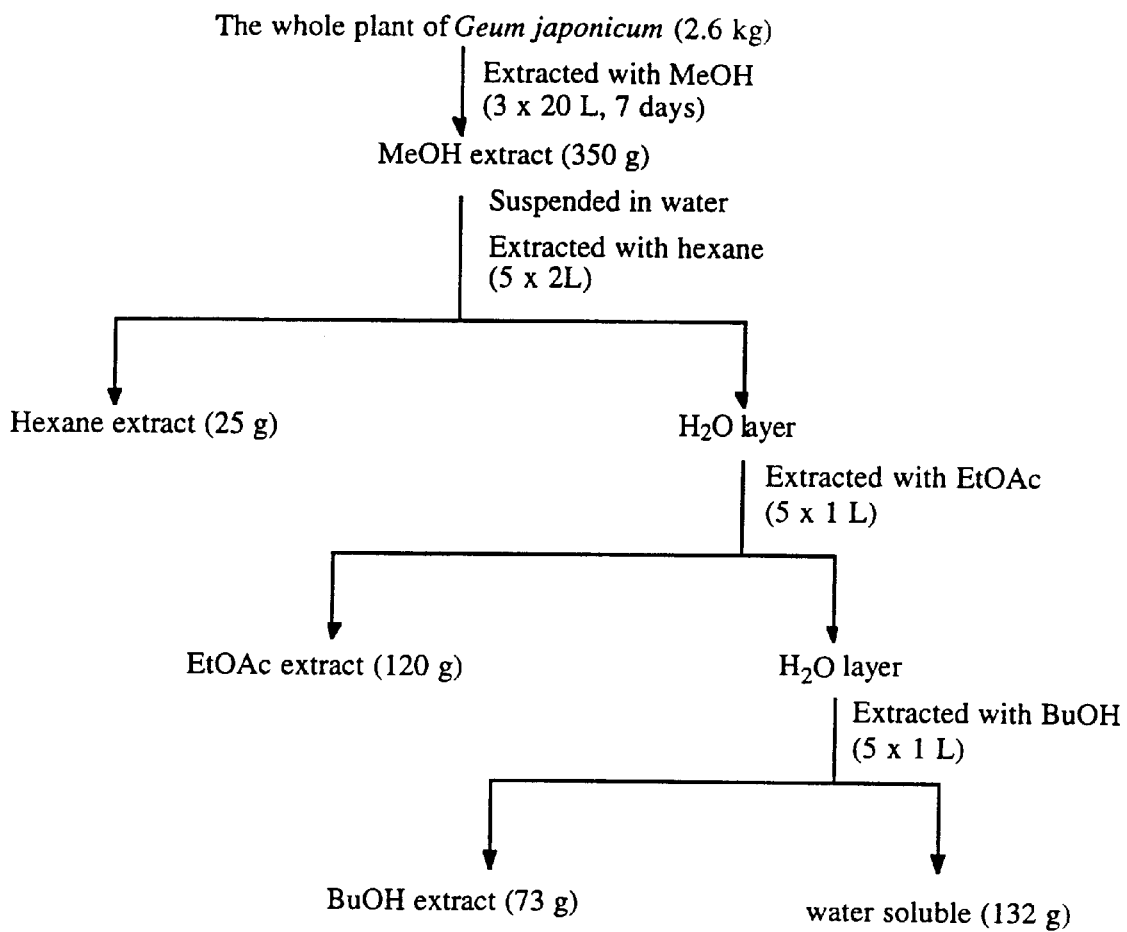
FIG. 12 is a schematic diagram showing the fractionation of the methanol extract from *G. japonicum.

This example describes the characterization of a methanol extract of the whole plant of *G. japonicum* which was found to show significant inhibitory activity against HIV-1 protease. In particular, a methanol extract of the whole plant of *G. japonicum* was successively partitioned into hexane, ethyl acetate and n-BuOH soluble fractions (FIG. 12). The biological evaluation of the extract and fractions indicated that most of the activity was in the ethyl acetate soluble fraction (Table 1)

MATERIALS AND METHODS

Thin layer chromatography (TLC) was carried out on silica gel pre-coated glass plates (J. T. Baker, Si254F, 250 μm layer thickness) and on $C_{18}$ silica pre-coated plates (Whatman, $KC_{18}F$, 200 μm). Analytical TLC plates were visualized using UV light and by spraying with ceric sulphate-$H_2SO_4$ or methanolic $FeCl_3$. Flash chromatography was carried out using Kieselgel 60 of mesh range 230–400 ASTM (Merck or J. T. Baker). For gel permeation column chromatography, sephadex LH 20 was used.

Optical rotations were determined on a automatic polarimeter. IR spectra were recorded on a Perkin Elmer 1600 Series FTIR spectrometer. EIMS were recorded on a MICROMASS 7035E mass spectrometer at 70 eV. All NMR spectra ($^1H$, $^{13}C$, COSY, NOE, HMQC and HMBC) were recorded on a Bruker AMX 500 spectrometer (500 MHz for $^1H$ and 125 MHz for $^{13}C$) in pyridine-$d_5$, the chemical shifts are reported in ppm with TMS as an internal standard and coupling constants (J) are given in Hz.

Plant Material

The whole plant of *Geum japonicum* used in this experiment was collected from China in August, 1994. The material was identified as *G. japonicum* Thunb. by Dr. Dao-Feng Chen, Department of Pharmacology, Shanghai Medical University, China. A voucher specimen was deposited in Department of Pharmacology, Shanghai University of Traditional Chinese Medicine, China.

Extraction and Isolation

Dried whole plants (2.6 kg) were chopped into small pieces and extracted three times with MeOH (20 liters) at room temperature for 7 days and the extract was evaporated in vacuo to yield MeOH extract (350 g). The MeOH extract was suspended in distilled water (1 l) and successively extracted with hexane (2 l×5), EtOAc (2 l×5) and n-BuOH 1 l×5). The EtOAc soluble fraction was filtered and the filtrate was evaporated under reduced pressure to give a brown oil (120 g).

Figure 13:
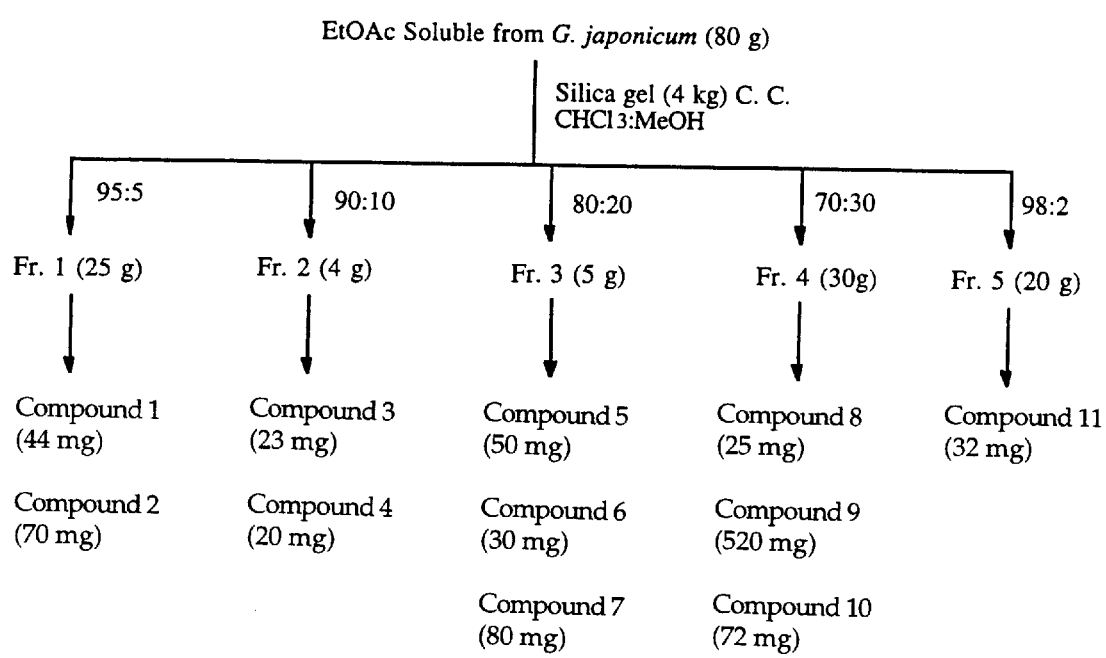
*
FIG. 13 is a schematic diagram showing the fractionation of the ethyl acetate soluble extract from *G. japonicum.

A portion of the EtOAc extract (80 g) was subjected to silica gel (2.0 kg) chromatography on a 120 mm i. d. column and eluted with a linear gradient $CHCl_3$-MeOH system (100:0 to 70:30). Fractions of 500 ml each were collected and examined on silica gel TLC ($CHCl_3$-MeOH, 9:1 and 7:3). Fractions with similar $R_f$ (TLC) were combined and concentrated to afford fractions 1 to 5 as shown in FIG. 13.

Fraction 1 (2.5 g) was further purified by rechromatography on silica gel (150 g) column of 50 mm i. d. and eluted with CHCl$_3$-MeOH (95:5) to yield a mixture of compound 1 and 3β-hydroxy-12-ursen-28-oic acid. The mixture was further purified by preparative TLC (CHCl$_3$-MeOH, 95:5) to give 2α,19α-dihydroxy-3-oxo-12-ursen-28-oic acid (1) (44 mg) and 3β-hydroxy-12-ursen-28-oic acid (2) (70 mg).

NMR and Other Physical Data for Compounds 1–11

2α,19α-Dihydroxy-3-oxo-12-ursen-28-oic acid (1)

A colourless powder [α]$_D$+1.7°(c 1.0, EtOH); mp 215–217° C.; C$_{30}$H$_{46}$O$_5$; HRMS:486.3373 (cald. for C$_{30}$H$_{46}$O$_5$, 486.3345); EIMS m/z: 486 (M), 438, 366, 246, 231, 221, 220, 219, 218, 205, 203, 202, 185, 146; IR KBr (cm$^{-1}$): 3600–3200, 2928, 2869, 1684, 1650, 1384, 1105; $^1$H-NMR (pyridine-d$_5$, 500 MHz): δ1.01 (3H, s, 24-H$_3$), 1.09 (3H, s, 26-H$_3$), 1.12 (3H, d, J=6.6 Hz, 30-H$_3$), 1.15 (3H, s, 25-H$_3$), 1.22 (3H, s, 23-H$_3$), 1.25 (1H, m, 5-H), 1.37 (1H, m, 1-H$_a$), 1.42 (3H, s, 29-H$_3$), 1.50 (1H, m, 20-H), 1.64 (3H, s, 27-H$_3$), 1.87 (1H, t, J=8.9 Hz, 9-H), 2.08 (1H, m, 21-H$_a$), 2.11 (1H, m, 22-H$_a$), 2.13 (1H, m, 21-H$_b$), 2.15 (1H, m, 22-H$_b$), 2.48 (1H, dd, J=12.5, 6.5 Hz, 1-H$_b$), 3.03 (1H, s, 18-H), 4.80 (1H, dd, J=12.5, 6.5 Hz, 2-H), 5.55 (1H, br s, 12-H). $^{13}$C-NMR (pyridine-d$_5$): δ=50.10 (t, C1), 69.73 (d, C2), 216.41 (s, C3), 48.10 (s, C4), 57.67 (d, C5), 19.55 (t, C6), 33.14 (t, C7), 40.37 (s, C8), 47.33 (d, C9), 37.90 (s, C10), 24.12 (t, C11), 127.55 (d, C12), 140.07 (s, C13), 42.16 (s, C14), 29.24 (t, C15), 26.31 (t, C16), 48.25 (s, C17), 54.56 (d, C18), 72.67 (s, C19), 42.35 (d, C20), 26.92 (t, C21), 38.45 (t, C22), 25.28 (q, C23), 21.77 (q, C24), 17.30 (q, C25), 16.77 (q, C26), 24.66 (q, C27), 180.65 (s, C28), 27.06 (q, C29), 15.95 (q, C30).

3β-Hydroxy-12-ursen-28-oic acid (2)

A colourless powder, [α]$_D$+65 (c 1.0, MeOH); mp 290–292° C.; C$_{30}$H$_{48}$O$_3$; EIMS m/z: 456 [M]$^+$, 410, 248, 203, 157; IR KBr (cm$^{-1}$): 3425, 1689, 1640; $^1$H-NMR (pyridine-d$_5$, 500 MHz): δ0.91 (3H, s, 24-H$_3$), 1.00 (6H, d, J=6.4 Hz, 29, 30-H$_3$), 1.02 (3H, s, 26-H$_3$), 1.06 (3H, s, 25-H$_3$), 1.24 (3H, s, 23-H$_3$), 1.29 (3H, s, 27-H$_3$), 2.65 (1H, s, 18-H), 3.46 (1H, t, J=7.9 Hz, 3-H), 5.50 (1H, br s, 12H). $^{13}$C-NMR (pyridine-d$_5$, 125 MHz): δ39.12 (t, C1), 28.13 (t, C2), 78.15 (d, C3), 39.39 (s, C4), 55.85 (d, C5), 18.81 (t, C6), 33.61 (t, C7), 40.00 (s, C8), 48.07 (d, C9), 37.31 (s, C10), 23.65 (t, C11), 125.66 (d, C12), 139.28 (s, C13), 42.53 (s, C14), 28.71 (t, C15), 24.93 (t, C16), 48.07 (s, C17), 53.57 (d, C18), 39.42 (s, C19), 39.51 (d, C20), 31.10 (t, C21), 37.45 (t, C22), 28.82 (q, C23), 15.70 (q, C24), 16.57 (q, C25), 17.48 (q, C26), 23.94 (q, C27), 179.87 (s, C28), 17.53 (q, C29), 21.43 (q, C30).

A portion of fraction 2 (3.0 g) was rechromatographed on a 30 mm i. d. column of silica gel (180.0 g) and eluted with CHCl$_3$:MeOH(90:10). Fractions of 15 ml each were collected and examined on silica gel TLC (CHCl$_3$-MeOH, 9:1). Fractions with similar R$_f$ (TLC) were combined and concentrated then by preparative TLC (CHCl$_3$-MeOH, 90:10) to give 3α,19α-dihydroxy-12-ursen-28-oic acid (3) (23 mg) and 2α,3β-dihydroxy-12-oleanen-28-oic acid (4) (20 mg).

3α,19α-Dihydroxy-12-ursen-28-oic acid (3)

A colourless powder, [α]$_D$+36.5 (c 1.5, Pyridine); mp 302–304° C.; C$_{30}$H$_{48}$O$_4$; EIMS m/z: 472 [M]$^+$, 454, 439, 426, 408, 393, 354, 219, 218, 146; IR KBr (cm$^{-1}$): 3427, 1695, 1630; $^1$H-NMR (pyridine-d$_5$, 500 MHz): δ0.92 (3H, s, 26-H$_3$), 1.03 (3H, s, 23-H$_3$), 1.12 (3H, s, 24-H$_3$), 1.17 (3H, d, J=6.4 Hz, 30-H$_3$), 1.24 (3H, s, 25-H$_3$), 1.45 (3H, s, 27-H$_3$), 1.73 (3H, s, 29-H$_3$), 3.07 (1H, s, 18H), 3.43 (1H, dd, j=3.0 Hz, 3-H), 5.61 (1H, br s, 12-H). $^{13}$C-NMR (pyridine-d$_5$, 125 MHz): δ=39.03 (t, C1), 28.12 (t, C2), 78.22 (d, C3), 39.39 (s, C4), 55.89 (d, C5), 18.96 (t, C6), 33.62 (t, C7), 40.39 (s, C8), 47.80 (d, C9), 37.37 (s, C10), 24.04 (t, C11), 128.06 (d, C12), 139.97 (s, C13), 42.13 (s, C14), 29.33 (t, C15), 26.43 (t, C16), 48.33 (s, C17), 54.65 (d, C18), 72.72 (s, C19), 42.38 (d, C20), 26.95 (t, C21), 38.50 (t, C22), 28.79 (q, C23), 17.24 (q, C24), 16.77 (q, C25), 16.51 (q, C26), 24.69 (q, C27), 180.72 (s, C28), 27.14 (q, C29), 15.58 (q, C30).

Acetylation of 3α,19α-dihydroxy-12-ursen-28-oic acid (3)

Compound 3 (15 mg) was dissolved in Ac$_2$O (1 ml) and dried pyridine (1 ml) and the reaction mixture was kept at 80° C. for 48 h. The reaction mixture was then poured into cold H$_2$O, extracted with EtOAc. The acetate was obtained (3a) (11.5 mg). IR KBr (cm$^{-1}$): 3425, 1735, 1690, 1630; $^1$H-NMR (CD$_3$OD, 500 MHz): δ0.82 (3H, s, 26-H$_3$), 0.89 (3H, s, 23-H$_3$), 0.90 (3H, s, 24-H$_3$), 0.94 (3H, d, J=6.7 Hz, 30-H$_3$), 0.99 (3H, s, 25-H$_3$), 1.20 (3H, s, 27-H$_3$), 1.36 (3H, s, 29-H$_3$), 2.04 (3H, s, COCH$_3$), 2.51 (1H, s, 18-H), 4.47 (1H, m, 3-H), 5.29 (1H, br s, 12-H).

2α,3β-Dihydroxy-12-oleanen-28-oic acid (4)

A colourless powder, [α]$_D$+30.5 (c 1.2, Pyridine); mp 263–265° C.; C$_{30}$H$_{48}$O$_4$; EIMS m/z: 472 [M]$^+$, 454, 426, 408, 248, 235, 233, 223, 219, 203, 189, 133; IR KBr (cm$^{-1}$): 3440, 1690; $^1$H-NMR (pyridine-d$_5$, 500 MHz): δ0.95 (3H, s, 26-H$_3$), 1.00 (3H, s, 23-H$_3$), 1.01 (3H, s, 24-H$_3$), 1.03 (3H, d, J=6.4 Hz, 30-H$_3$), 1.08 (3H, s, 25-H$_3$), 1.27 (3H, s, 27-H$_3$), 2.25 (1H, dd, J=14, 4 Hz, 18-H), 3.40 (1H, d, J=10 Hz, 3-H), 4.10 (1H, dd, J=10, 10, 4.0 Hz, 2-H), 5.25 (1H, br t, J=4 Hz, 12-H). $^{13}$C-NMR (pyridine-d$_5$, 125 MHz): δ=46.42 (t, C1), 68.55 (d, C2), 83.78 (d, C3), 39.80 (s, C4), 55.88 (d, C5), 18.81 (t, C6), 33.18 (t, C7) 39.80 (s, C8), 48.13 (d, C9), 38.51 (s, C10), 23.73 (t, C11), 122.43 (d, C12), 144.81 (s, C13), 41.96 (s, C14), 28.24 (t, C15), 23.89 (t, C16), 47.71 (s, C17), 42.18 (d, C18), 46.63 (t, C19), 30.91 (s, C20), 34.19 (t, C21), 33.18 (t, C22), 29.30 (q, C23), 17.44 (q, C24), 16.81 (q, C25), 17.62 (q, C26), 26.13 (q, C27), 180.13 (s, C28), 33.18 (q, C29), 23.66 (q, C30).

Fraction 3 (4.5 g) was purified on a column of silica gel (250 g) and eluted with CHCl$_3$-MeOH=80:20. Fractions of 15 ml each were collected and examined on silica gel TLC (CHCl$_3$-MeOH, 8:2). Fractions with similar R$_f$ (TLC) were combined and concentrated to afford afford two fractions A and B. Fraction A was purified by preparative TLC (Ethyl ether-Acetone, 7:3) to give 2α,3α,19α-trihydroxy-12-ursen-28-oic acid (5) (50 mg) and 2α,3β,19α-trihydroxy-12-ursen-28-oic acid (6) (30 mg), and fraction B (0.21 g) was purified by further silica gel (20.0 g) chromatography and eluted with Ethyl ether-EtOAc (6:4) to yield 2α,3β,19α,23-tetrahydroxy-12-ursen-28-oic acid (7) (80 mg).

2α,3α,19α-Trihydroxy-12-ursen-28-oic acid (5)

A colourless powder, [α]$_D$+12.0 (c 1.0, Pyridine); mp 270° C.; C$_{30}$H$_{48}$O$_5$; EIMS m/z: 488 [M]$^+$, 470, 452, 442, 424, 370, 352, 293, 246, 219, 218, 146; IR KBr (cm$^{-1}$): 3400, 1690, 1630, 820, 805; $^1$H-NMR (pyridine-d$_5$, 500 MHz): δ0.92 (3H, s, 26-H$_3$), 1.03 (3H, s, 23-H$_3$), 1.12 (3H, s, 24-H$_3$), 1.17 (3H, d, J=6.4 Hz, 30-H$_3$), 1.24 (3H, s, 25-H$_3$), 1.45 (3H, s, 27-H$_3$), 1.73 (3H, s, 29-H$_3$), 3.07 (1H, s, 18-H), 3.43 (1H, dd, J=12.1, 5.0 Hz, 2-H), 5.61 (1H, br s, 12-H). $^{13}$C-NMR (pyridine-d$_5$, 125 MHz): δ=42.20 (t, C1), 66.08 (d, C2), 79.34 (d, C3), 38.68 (s, C4), 48.80 (d, C5), 18.62(t, C6), 33.55 (t, C7), 40.61 (s, C8), 47.65 (d, C9), 38.80 (s, C10), 24.09 (t, C11), 128.01 (d, C12), 139.96 (s, C13), 42.37 (s C14), 29.44 (t, C15), 26.40 (t, C16), 48.29 (s, C17), 54.61 (d, C18), 72.71 (s, C19), 42.89 (d, C20), 27.09 (t, C21), 38.49 (t, C22), 29.26 (q, C23), 22.28 (q, C24), 16.77 (q, C25), 17.29 (q, C26), 24.64 (q, C27), 180.64 (s, C28), 26.96 (q, C29), 16.65 (q, C30).

2α,3β,19α-Trihydroxy-12-ursen-28-oic acid (6)

A colourless powder, $[\alpha]_D$-20 (c 0.8, Pyridine); mp 272–274° C.; $C_{30}H_{48}O_5$; EIMS m/z: 488 [M]$^+$, 470, 452, 370, 264, 246, 218, 146; IR KBr (cm$^{-1}$): 3450, 1690; $^1$H-NMR (pyridine-d$_5$, 500 MHz): δ0.82 (3H, s, 26-H$_3$), 0.87 (3H, s, 23-H$_3$), 0.93 (3H, s, 24-H$_3$), 1.05 (3H, d, J=6.4 Hz, 30-H$_3$), 1.24 (3H, s, 25-H$_3$), 1.45 (3H, s, 27-H$_3$), 1.73 (3H, s, 29-H$_3$), 3.07 (1H, s, 18-H), 3.43 (1H, dd, J=12.1, 5.0 Hz, 2-H), 5.61 (1H, br s, 12-H). $^{13}$C-NMR (pyridine-d$_5$, 125 MHz): δ=48.00 (t, C1), 68.93 (d, C2), 83.91 (d, C3), 38.23 (s, C4), 55.51 (d, C5), 18.92 (t, C6), 33.56 (t, C7), 40.72 (s, C8), 47.85 (d, C9), 39.31 (s, C10), 24.32 (t, C11), 128.00 (d, C12), 139.95 (s, C13), 42.12 (s, C14), 28.91 (t, C15), 26.52 (t, C16), 48.21 (s, C17), 54.52 (d, C18), 72.21 (s, C19), 42.01 (d, C20), 25.95 (t, C21), 38.05 (t, C22), 28.93 (q, C23), 16.41 (q, C24), 16.76 (q, C25), 17.43 (q, C26), 24.52 (q, C27), 180.52 (s, C28), 27.62 (q, C29), 17.15 (q, C30).

2α,3β,19α,23-Tetrahydroxy-12-ursen-28-oic acid (7)

A colourless powder, $[\alpha]_D$+18.6 (c 0.9, Pyridine); mp 301–304° C.; $C_{30}H_{48}O_6$; EIMS m/z: 504 [M]$^+$, 264, 246, 219, 201; IR KBr (cm$^{-1}$): 3400, 1700, 1630, 835; $^1$H-NMR (pyridine-$_5$, 500 MHz): δ1.06 (3H, s, 26-H$_3$), 1.09 (3H, s, 24-H$_3$), 1.11 (3H, d, J=6.0 Hz, 30-H$_3$), 1.12 (3H, s, 25-H$_3$), 1.42 (3H, s, 27-H$_3$), 1.65 (3H, s, 29-H$_3$), 3.03 (1H, s, 18-H), 3.40 (1H, d, J=9.5, 3-H), 3.71 (1H, d, J=10.1, 23-H$_a$), 4.17 (1H, d, J=10.1, 23-H$_b$), 4.24 (1H, t, J=11.0, 9.5 Hz, 2-H), 5.57 (1H, br s, 12-H). $^{13}$C-NMR (pyridine-d$_5$, 125 MHz): δ=47.85 (t, C1), 68.87 (d, C2), 78.34 (d, C3), 43.62 (s, C4), 48.04 (d, C5), 18.69 (t, C6), 33.20 (t, C7), 40.47 (s, C8), 47.84 (d, C9), 38.40 (s, C10), 24.17 (t, C11), 127.95 (d, C12), 140.03 (s, C13), 42.18 (s, C14), 29.29 (t, C15), 26.40 (t, C16), 48.29 (s, C17), 54.61 (d, C18), 72.71 (s, C19), 42.36 (d, C20), 26.96 (t, C21), 38.51 (t, C22), 66.66 (t, C23), 14.31 (q, C24), 17.34 (q, C25), 17.40 (q, C26), 24.69 (q, C27), 180.83 (s, C28), 27.12 (q, C29), 16.78 (q, C30).

A portion of fraction 4 (3.0 g) was subjected sephadex LH 20 (50.0 g) and eluted with H$_2$O-MeOH gradient to give 28-D-glucoside of 2α,3β,19α-trihydroxy-12-ursen-28-oic acid (8) (25 mg), 28-D-glucoside of 2α,3β,19α,23-tetrahydroxy-12-ursen-28-oic acid (10) (520 mg) and 3β-D-glucoside-β-sitosterol (11) (72 mg).

28-D-glucoside of 2α,3β,19α-trihydroxy-12-ursen-28-oic acid (8)

Colourless needles, $[\alpha]_D$+36.5 (c 1.5, Pyridine); mp 302–304° C.; $C_{36}H_{56}O_4$; EIMS m/z: 488 (M$^+$-C$_6$H$_{10}$O$_5$), 470, 452, 442, 424, 246, 198, 173, 146; IR KBr (cm$^{-1}$): 3400, 1680, 1640; $^1$H-NMR (pyridine-d$_5$, 500 MHz): δ1.07 (3H, d, J=7.5 Hz, 30-H$_3$), 1.05, 1.08, 1.19, 1.25, 1.40, 1.66 (each 3H, 23–29-H$_3$), 2.92 (1H, s, 18-H), 3.38 (1H, d, J=9.3 Hz, 3-H), 4.07 (1H, m, 2-H), 4.12–4.51 (sugar protons), 5.53 (1H, br s, 12-H), -H), 6.26 (1H, d, J=8.1 Hz, 1'-H). $^{13}$C-NMR (pyridine-d$_5$, 125 MHz): δ=47.97 (t, C1), 68.65 (d, C2), 83.82 (d, C3), 38.48 (s, C4), 55.95 (d, C5), 19.03 (t, C6), 33.49 (t, C7), 40.60 (s, C8), 47.84 (d, C9), 39.82 (s, C10), 24.16 (t, C11). 128.35 (d, C12), 139.25 (s, C13), 42.12 (s, C14), 29.18 (t, C15), 26.68 (t, C16), 48.62 (s, C17), 54.39 (d, C18), 72.66 (s, C19), 42.12 (d, C20), 26.09 (t, C21), 37.69 (t, C22), 29.33 (q, C23), 16.68 (q, C24), 16.96 (q, C25), 17.63 (q, C26), 24.56 (q, C27), 177.03 (s, C28), 27.01 (q, C29), 17.45 (q, C30), 95.80 (d, C1'), 74.00 (d, C2'), 78.86 (d, C3'), 71.24 (d, C4'), 79.17 (d, C5'), 62.35 (t, C6').

Alkaline hydrolysis of compound 8

Compound 8 (10 mg) was added to a solution prepared from methanol (2.5 ml), water (1.5 ml) and potassium hydroxide (100 mg). The resulting mixture was heated under reflux for 4 h, poured into water, acidified by addition of hydrochloric acid, and extracted with ethyl acetate 30 ml×3.

From the ethyl acetate layer, aglycone (6 mg) was identified as tormentic acid by comparison of $^1$H and $^{13}$C-NMR data with the those of compound 6.

28-D-glucoside of 2α,3β,19α,23-tetrahydroxy-12-ursen-28-oic acid (9)

Colourless needles, $[\alpha]_D$+36.5 (c 1.2, Pyridine); mp 235–237° C.; $C_{36}H_{58}O_{11}$; EIMS m/z: 504 (M$^+$-C$_6$H$_{10}$O$_5$), 264, 246, 219, 201; IR KBr (cm$^{-1}$): 3407, 1685, 1620; $^1$H-NMR (pyridine-d$_5$, 500 MHz): δ1.06 (3H, d, J=6.5 Hz, 30-H$_3$), 1.09, 1.15, 1.25, 1.37, 1.62 (each 3H, 24–29 H$_3$), 2.92 (1H, s, 18-H), 3.71 (1H, d, J=10.5 Hz, 3-H), 4.07 (1H, m, 2-H), 4.13–4.50 (sugar protons), 5.54 (1H, br s, 12-H), 6.30 (1H, d, J=8.1 Hz, 1'-H). $^{13}$C-NMR (pyridine-d$_5$, 125 MHz): δ=47.98 (t, C1), 68.95 (d, C2), 78.39 (d, C3), 43.63 (s, C4), 48.03 (d, C5), 18.76 (t, C6), 33.19 (t, C7), 40.68 (s, C8), 47.89 (d, C9), 38.42 (s, C10), 24.24 (t, C11), 128.41 (d, C12), 139.32 (s, C13), 42.13 (s, C14), 29.23 (t, C15), 26.13 (t, C16), 48.64 (s, C17), 54.44 (d, C18), 72.67 (s, C19), 42.20 (d, C20), 26.72 (t, C21), 37.74 (t, C22), 66.66 (t, C23), 14.35 (q, C24), 17.52 (q, C25), 17.56 (q, C26), 24.56 (q, C27), 177.00 (s, C28), 27.00 (q, C29), 16.71 (q, C30), 95.85 (d, C1'), 74.08 (d, C2'), 79.25 (d, C3'), 71.29 (d, C4'), 78.97 (d, C5'), 62.40 (t, C6').

Alkaline hydrolysis of compound 9

Compound 9 (20 mg) was added to a solution prepared from methanol (2.5 ml), water (1.5 ml) and potassium hydroxide (150 mg). The resulting mixture was heated under reflux for 4 h, poured into water, acidified by addition of hydrochloric acid, and extracted with ethyl acetate (30 ml×3). From the ethyl acetate layer, the aglycone (14 mg) was identified as 19-hydroxy-asiatic acid by comparison of $^1$H and $^{13}$C-NMR data with the those of compound 7.

3-D-glucopyranosyl-sitosterol (10)

Colourless needles, $C_{35}H_{60}O_6$; $^{13}$C-NMR (pyridine-d$_5$, 125 MHz): δ=37.47 (t, C1), 30.15 (t, C2), 78.11 (d, C3), 39.97 (t, C4), 140.88 (d, C5), 121.85 (d, C6), 32.16 (t, C7), 32.06 (d, C8), 50.35 (d, C9), 36.89 (s, C10), 21.27 (t, C11), 39.24 (t, C12), 42.49 (s, C13), 56.86 (d, C14), 24.50 (t, C15), 28.52 (t, C16), 56.26 (d, C17), 12.18 (q, C18), 19.42 (q, C19), 36.36 (d, C20), 19.03 (q, C21), 34.21 (t, C22), 26.41 (t, C23), 46.05 (d, C24), 29.47 (d, C25), 19.99 (q, C26), 19.25 (q, C27), 23.39 (d, C28), 12.01 (q, C29), 102.42 (d, C1'), 75.06 (d, C2'), 78.24 (d, C3'), 71.57 (d, C4'), 78.29 (d, C5'), 62.71 (t, C6').

Fraction 5 was chromatographed on a silica gel column (hexane: EtOAc(8:2) to give β-sitosterol (11) (25 mg).

Biological Assay

Recombinant HIV-1 protease was prepared from the expression vector, PGEX-PR 107, in *E. coli* DII5a and was purified according to the method established in Dr. Wan's laboratory [14].

The proteolytic activity of HIV-1 PR was measured by Dr. Wan's group at the Biochemistry Department using the synthetic heptapeptide Ser-Gln-Asn-Tyr-Pro-Ile-Val (SQNYPIV), corresponding to the p24-p17 cleavage site in the natural gag precursor, as substrate. The products of cleavage were analyzed by reversed-phase high-performance liquid chromatography (RP-HPLC, Ultrasphere ODS, 5μ, 4.6 mm×15 cm, Beckman, Calif., USA) with a 7–33% acetonitrile gradient in 0.1% trifluoroacetic acid (TFA). Product peak areas were integrated by a data system (Chromatopac C-R3A, Shimadzu, Japan) and compared with the standard peptide SQNY, which is expected to be generated from heptapeptide SQNYPIV after HIV-1 protease digestion. The extinction coefficient of the peptide SQNY was used to estimate the rate of proteolysis of the heptapeptide substrate. The assay was performed in a volume of 140 μl containing 90 pmole of substrate, 2 U of HIV-1 protease and compound solution in 0.1 M NaOAc buffer, pH 5.5, with 1 M $(NH_4)_2SO_4$, at 37° C. The reaction which proceeded for 2 h was terminated by the addition of 20 μl of aqueous 10% trifluoroacetic acid. The supernatant obtained by centrifuging at 12,000 rpm for 3 min was then analyzed by the hplc method. The unit of enzyme activity was defined as the amount of enzyme which yields 1 nmol of tetrapeptide SQNY under the above conditions in 1 min.

The proteolytic activity of HIV-1 protease inhibited by the compound was calculated as the activity of the control subtracting that of the sample, and then divided by itself.

RESULTS

Isolation and Structure Determination of the Compounds from *Geum japonicum*

The active EtOAc soluble fraction was subjected to silica gel column chromatography to give five fractions (FIG. 13). Further silica gel and sephadex LH 20 column gave a new triterpene acid, 2-alpha-19-alpha-dihydroxy-3-oxo-12-ursen-28-oic acid (1) together with eight known triterpenes, ursolic acid (2), epipomolic acid (3), maslinic acid (4), euscaphic acid (5), tormentic acid (6), 19-hydroxyasiatic acid (7), 28-D-glucoside of tormentic acid (8) and 28-D-glucoside-19-hydroxyasiatic acid (9) as well as 3-D-glucoside-sitosterol (10) and -sitosterol (11). The structures of these compounds were elucidated by various spectroscopic means and are shown in FIGS. 1–10.

1. 2α,19α-Dihydroxy-3-oxo-12-ursen-28-oic acid (1)

Compound (1) was obtained as a colourless powder. The IR spectrum indicated the presence of hydroxyl group (3600-3200 $cm^{-1}$), carboxylic acid group (1684 $cm^{-1}$), and double bond (1650 $cm^{-1}$). Its molecular formula was determined to be $C_{30}H_{46}O_5$ by high-resolution mass spectroscopy ($M^+$ 486.3373).

The $^{13}C$-NMR together with DEPT spectrum revealed thirty carbon signals including characteristic signals due to a trisubstituted double bond [δ127.55 (d) and 140.07 (s)], a carboxylic acid group (δ180.65), a ketone carbonyl group (δ216.41) and two alcoholic carbons [δ69.73 (d) and 72.67 (s)]. The $^1H$-NMR spectrum showed the presence of a hydroxy methine proton at δ4.80 (1H, dd, J=12.5, 6.5 Hz), an olefinic proton at δ5.55 (1H, br s), six singlets at δ1.01 (3H), 1.09 (3H), 1.15 (3H), 1.22 (3H), 1.42 (3H), 1.64 (3H) for six tertiary methyl group, and a doublet at δ1.12 (3H, d, J=6.6 Hz) for a secondary methyl group. The secondary methyl signal on ring E provides a most useful indicator for the presence of an urs-12-ene skeleton. In addition, the signals in its $^{13}C$-NMR at δ127.55 (d) and 140.07 (s) are characteristic for C-12/C-13 double bond in the ursene type structure [15–18]. The presence of the ursene skeleton was further verified using 2D NMR spectroscopy including HMBC measurement. The $^1H$-$^{13}C$ long-range COSY and $^1H$-$^1H$ COSY spectrum of this compound gave very good information for establishing the assignment of the partial structure of C-1 to C-3 carbons. There were long range correlations between H-2 proton at δ4.80 and the methylene carbon at δ50.10 (C-1) in the HMBC spectrum, and a cross-peak between the signals of H-2 proton and H-1 proton in $^1$-$^1H$ COSY spectrum, which indicated that the ketone carbonyl group must be either at position C-1 or C-3. Furthermore, the observation of the correlation between the ketone carbonyl group and two methyl carbons (C-23 at δ25.28 and C-24 at δ21.77) suggested the ketone must be at C-3 position. The secondary hydroxyl group was assigned to C-2 due to the correlation between the C-1 methylene carbon at δ50.10 and the C-25 methyl group. Splitting patterns for the hydroxyl methine proton (δ4.80, dd, J=12.5, 6.5 Hz) showed that the hydroxyl group is equatorial. The stereochemistry of the hydroxyl group was further confirmed by NOE experiments. In particular, on irradiation of signal of H-2 proton at δ4.80, the NOE effect was observed on the H-24 at δ1.01 and H-25 at δ1.15 methyl protons. Furthermore, irradiation of the signal of the H-25 methyl protons gave the NOE enhancements for H-26 methyl protons at δ1.09, H-24 methyl protons and H-2 proton. These data clearly suggested the equatorial configuration of the C-2 hydroxy group, as indicated in structure. On the other hand, a signal at δ3.03 (1H, s, H-18) assigned to the bridgehead H-18 suggested the presence of a 19-O-substituted urs-12-ene skeleton [19]. The hydroxy group at C-19 was assigned to the α position by analogy with the $^{13}C$-NMR chemical shifts of similarly substituted triterpene acids [20]. The carboxylic acid group was assigned to C-17 on the basis of a HMBC correlation to H-18.

Figure 14:
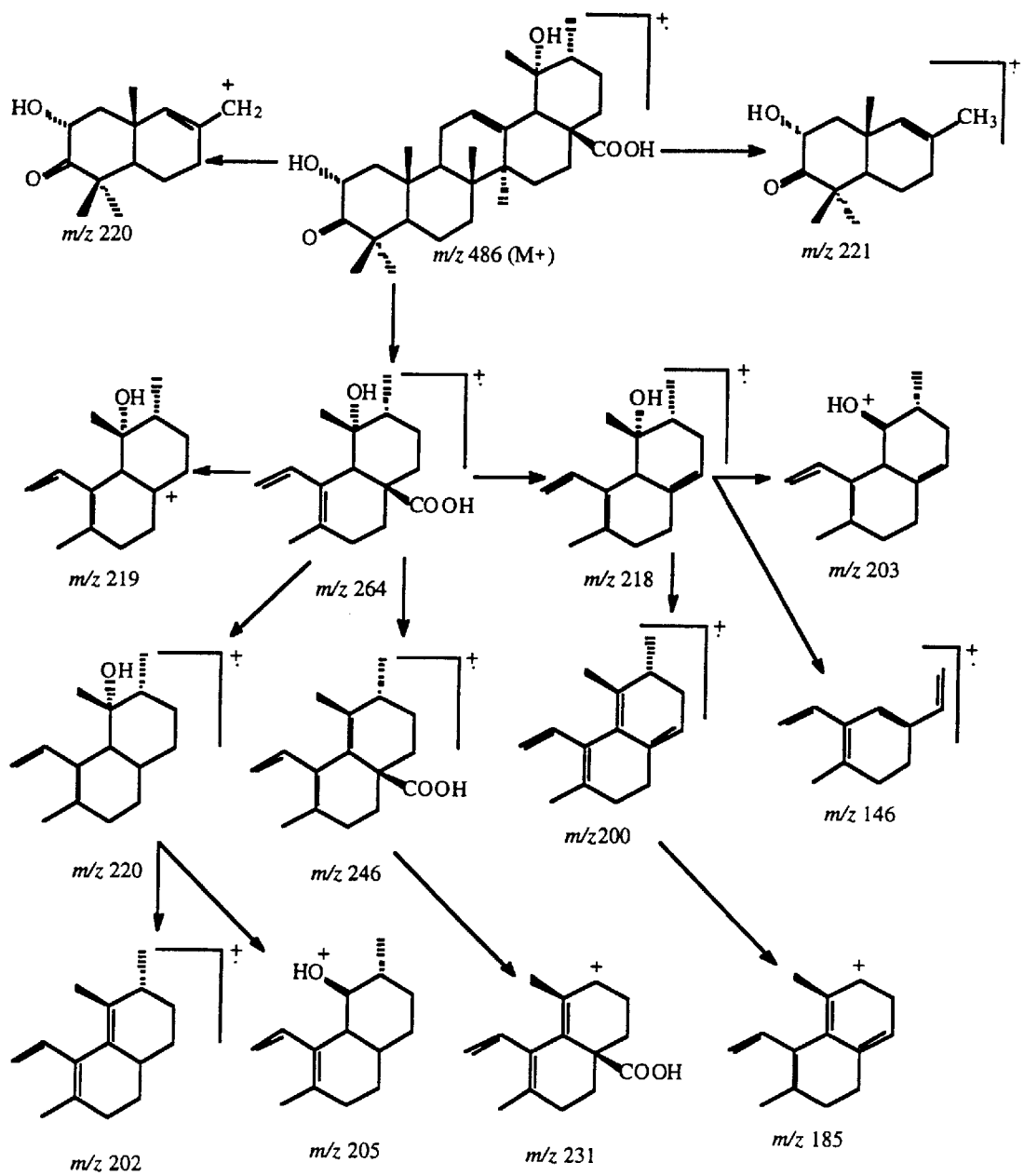
*
FIG. 14 is a schematic diagram showing the mass fragmentations of compound 1.

Furthermore, the structure of compound 1 was supported by analysis of ion peaks in the mass spectrum. The peaks at m/z 246 [264 —$H_2O$]$^+$, 220 [264 —$CO_2$]$^+$, 219 [264 —$CO_2H$]$^+$ and 218 [264 —$HCO_2H$]$^+$ corresponded to the typical retro-Diels-Alder (R. D. A.) cleavage fragments commonly found in the spectra of urs-12-ene derivatives possessing a carboxyl group on C-17 and a hydroxyl substituent on ring D or E. Besides, there was a base peak at m/z 146 apparently due to the secondary retro-Diels-Alder cleavage of the m/z 218 fragment ion. These fragmentations resemble very closely those of tormentic acid [21]. Other important ions were at m/z 438, 366 and 220 which indicated that a secondary hydroxy group and a ketone group were located in the A/B ring portion (FIG. 14).

Figure 1:
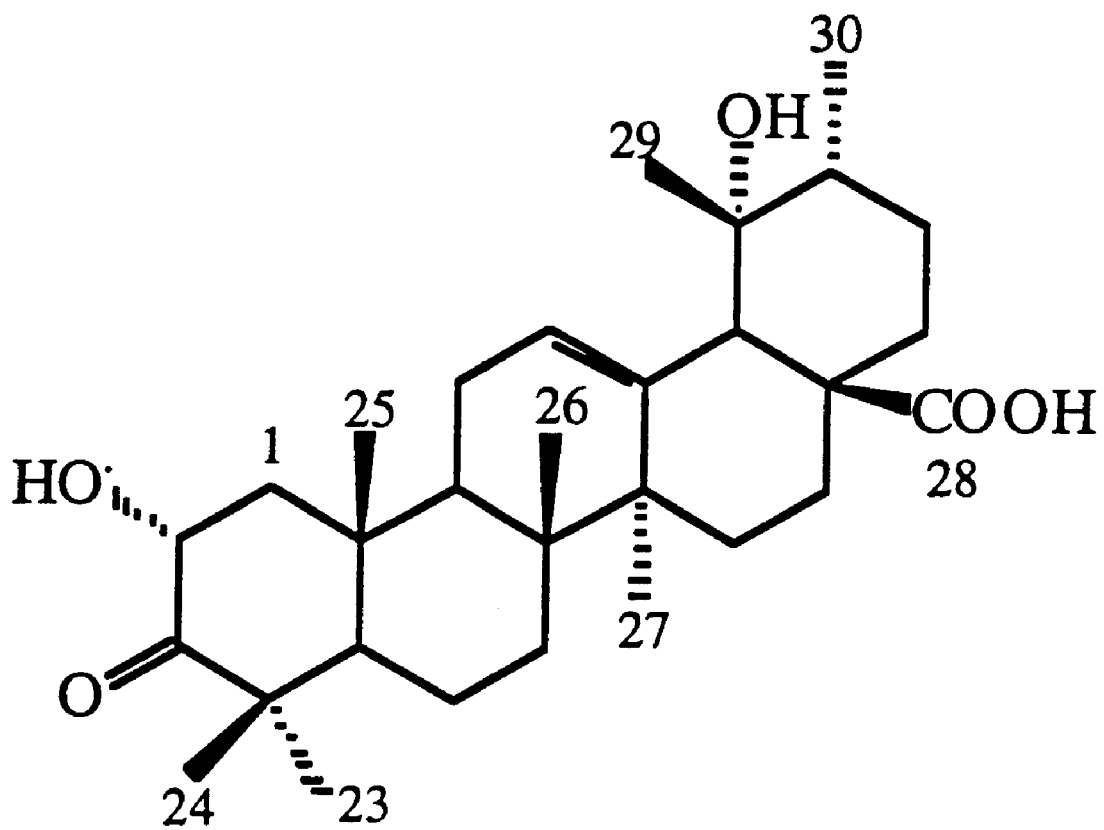
FIG. 1 shows the chemical formula of compound 1.

The complete assignment of all the carbons was determined (Table 2) with the help of DEPT, $^1H$-$^1H$ COSY, $^1H$-$^{13}C$ COSY, NOE and followed by analysis of the HMBC spectral data (Table 3). Based on all above information, compound 1 was found to be a new triterpene acid, and the structure of the natural product was formulated as 2α,19α-dihydroxy-3-oxo-12-ursen-28-oic acid as shown in FIG. 1.

2. Ursolic acid (2)

Compound 2 was obtained as a colourless powder mp 290–292° C., $[α]_D$+65 (MeOH, c 1.0). Its IR spectrum showed the presence of hydroxy group (3425 $cm^{-1}$), carboxylic acid group (1689 $cm^{-1}$) and olefinic group (1640 $cm^{-1}$). The molecular formula of compound 2 was determined to be $C_{30}H_{48}O_3$ by mass spectromscopy.

The $^{13}C$-NMR together with DEPT spectrum revealed thirty carbon signals including characteristic signals due to a trisubstituted double bond [125.66 (d) and 139.28 (s)], a carboxylic acid group [179.87 (s)] and a hydroxy methine carbon [78.15 (d)]. The $^1H$-NMR spectrum showed the presence of a hydroxy methine proton at 3.46 (1H, t, J=7.9 Hz) an olefinic proton at 5.50 (1H, br s), five singlets at 0.91 (3H), 1.02 (3H), 1.06 (3H), 1.24 (3H), 1.29 (3H) for five tertiary methyl groups and two doublets at 1.00 (6H, d, J=6.0 Hz) for two secondary methyl groups. The secondary methyl groups at ring E and the signals in its $^{13}C$-NMR at 125.66 (s) and 139.28 (s) are characteristic for C12/C-13 double bond in ursene-type structure. The splitting pattern of the hydroxy methine proton supported the equatorial 3-hydroxy group.

Figure 2:
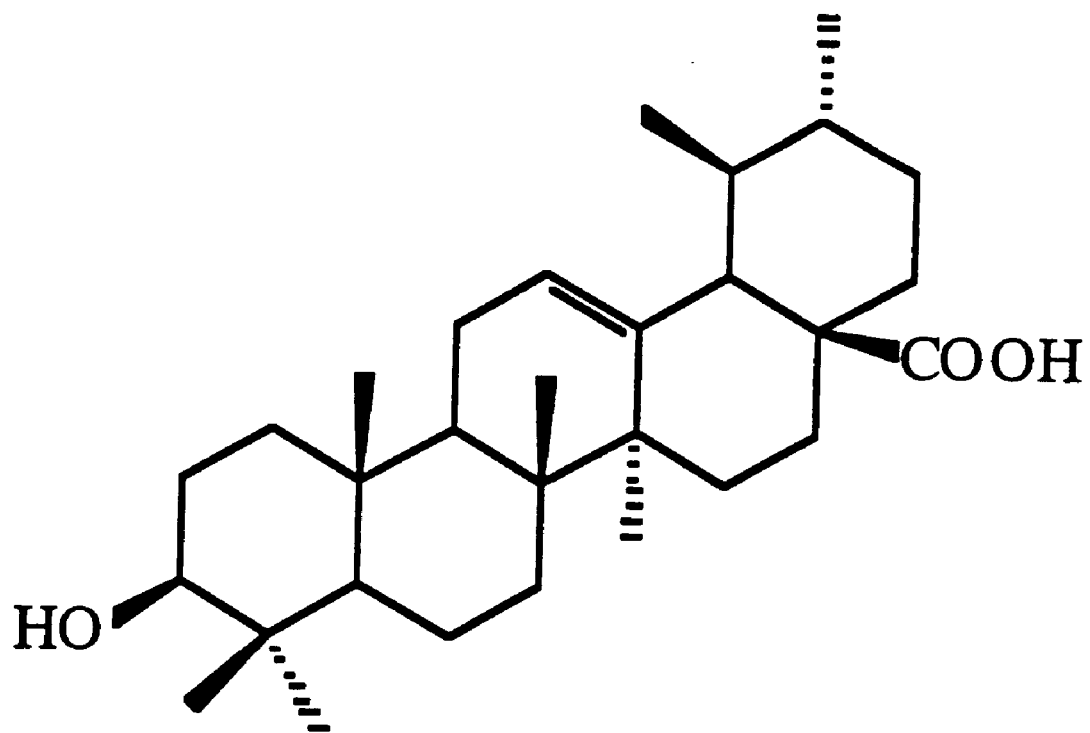
FIG. 2 shows the chemical formula of compound 2.

The mass spectrum was similar to that of ursolic acid and exhibited peaks at m/z 456 [M]$^+$, 410 [M-HCOOH]$^+$, 248, 203 [248-COOH]$^+$ and 157. By direct comparision of data (NMR, IR, mp and MS) with those reported in the literature [15], compound 20 was identified to be ursolic acid as shown in FIG. 2.

3. 3,19-Dihydroxy-12-ursen-28-oic acid (3)

Compound 3 was obtained as a colourless powder, $[\alpha]_D$+36.5. Its IR spectrum showed bands for hydroxy (3427 $cm^{-1}$), carbonyl (1695 $cm^{-1}$), and olefin (1630 $cm^{-1}$) absorptions. On acetylation with acetic anhydride, it formed a mono-acetate (3a). The molecular formula of compound 3 was determined to be $C_{30}H_{48}O_4$ by mass spectroscopy ($M^+$ 472.3). Compound 3 showed diagnostically important peaks at m/z 246, 218, 207, 146 due to retro-Diels-Alder fragmentation around ring C, which are consistent with the fragmentation pattern characteristic for the amyrin series [22]. From the above mass spectral fragments, it was also evident that the secondly hydroxyl group was present in the A/B ring portion and its location at C-3 was highly probable on a biogenetic basis [23]. The $^1$H-NMR spectrum of 3 exhibited signals for six tertiary methyl groups, one proton singlet at 3.06 (18-11), and one proton multiplet at 5.61. (12-H), as expected for an 12-ursen skeleton bearing an with alpha-hydroxy at C-19 [24–25]. Also, it showed a triplet-like signal centered at 3.43 (1H, t, J=3 Hz, 3-H), whose chemical shift and splitting pattern were typical of a 3-alpha-hydroxy group [26].

Figure 3:
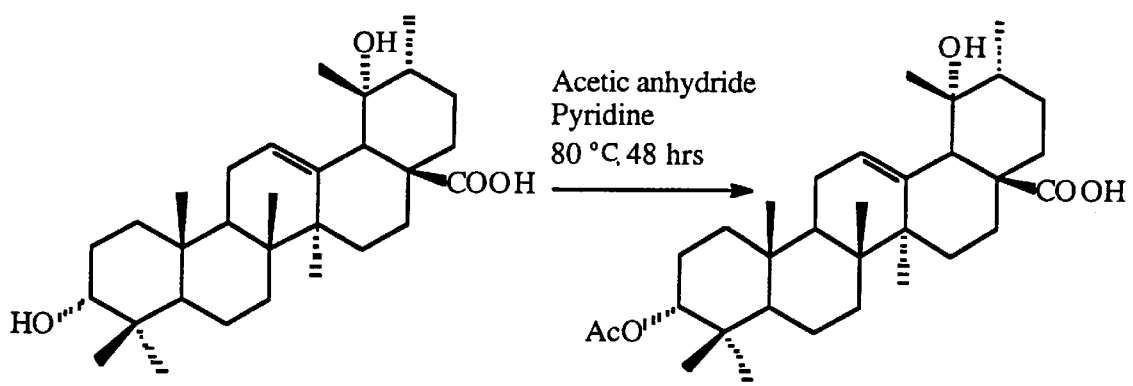
FIG. 3 shows the chemical formula of compound 3.

The $^{13}$C-NMR together with DEPT spectrum revealed thirty carbon signals including characteristic signals due to a trisubstituted double bond [$\delta$128.06 (d) and 139.98 (s)], a carboxylic acid group ($\delta$180.72) and two alcoholic carbons [$\delta$78.22 (d) and 72.72 (s)]. By direct comparison of data (NMR, IR, mp and MS) with those reported in the literature [27], compound 3 was identified to be 3,19-dihydroxy-12-ursen-28-oic acid as shown in FIG. 3.

4. Maslinic acid (4)

Compound 4 was obtained as a colourless powder, mp 263–265° C., $[\alpha]_D$+42.5 (pyridine, c 1.2), $C_{30}H_{48}O_4$ $[M]^+$, Its IR spectrum showed bands for hydroxy (3440 $cm^{-1}$), carboxylic acid (1690 $cm^{-1}$), and olefinic (1630 $cm^{-1}$) absorptions.

Figure 4:
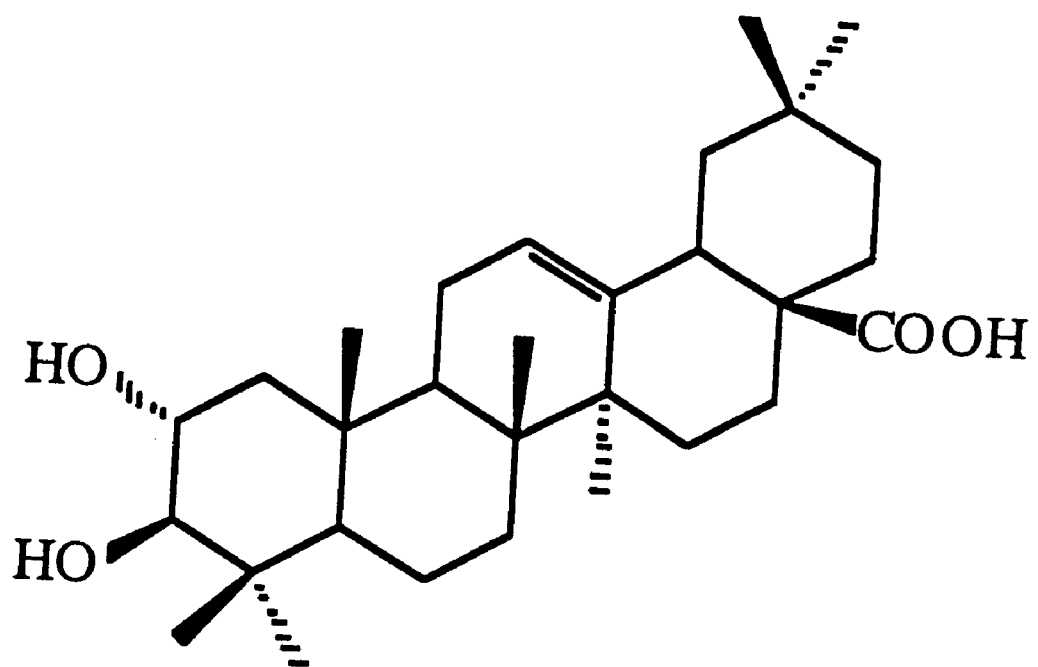
FIG. 4 shows the chemical formula of compound 4.

The $^1$H-NMR spectrum of 4 exhibited signals for seven tertiary methyl groups, one proton multiplet at 2.25 (1H, dd, J=14, 4 Hz, 18-H) and one proton multiplet at 5.25 (1H, br t, J=4 Hz, 12-H), as expected for an 12-oleanene skeleton. The $^{13}$C-NMR together with DEPT spectrum revealed thirty carbon signals including characteristic signals due to a trisubstituted double bond [$\delta$122.43 (d) and 144.81 (s)], a carboxylic acid group ($\delta$180.13) and two alcoholic carbons [$\delta$68.55 (d) and 83.78 (s)]. By direct comparison of data (NMR, IR, mp and MS) with those reported in the literature [28], compound 4 was identified to be maslinic acid as shown in FIG. 4.

5. 2,3,19-Trihydroxy-12-ursen-28-oic acid (5)

Compound 5 is a colourless powder, mp 270° C., $[\alpha]_D$+12 (c 1.0, MeOH). Its IR spectrum showed a hydroxyl group (3400 $cm^{-1}$), carboxylic acid group (1690 $cm^{-1}$) and a trisubstituted double bond (1630, 820, 805 $cm^{-1}$). Its mass spectrum showed characteristic fragments at m/z 264 (a), 219 (b), 146 (c), 370 (d). These observations indicated that the basic skeleton of compound 5 was a 12-ursen-28-oic acid possessing one hydroxyl group at C-19.

Figure 5:
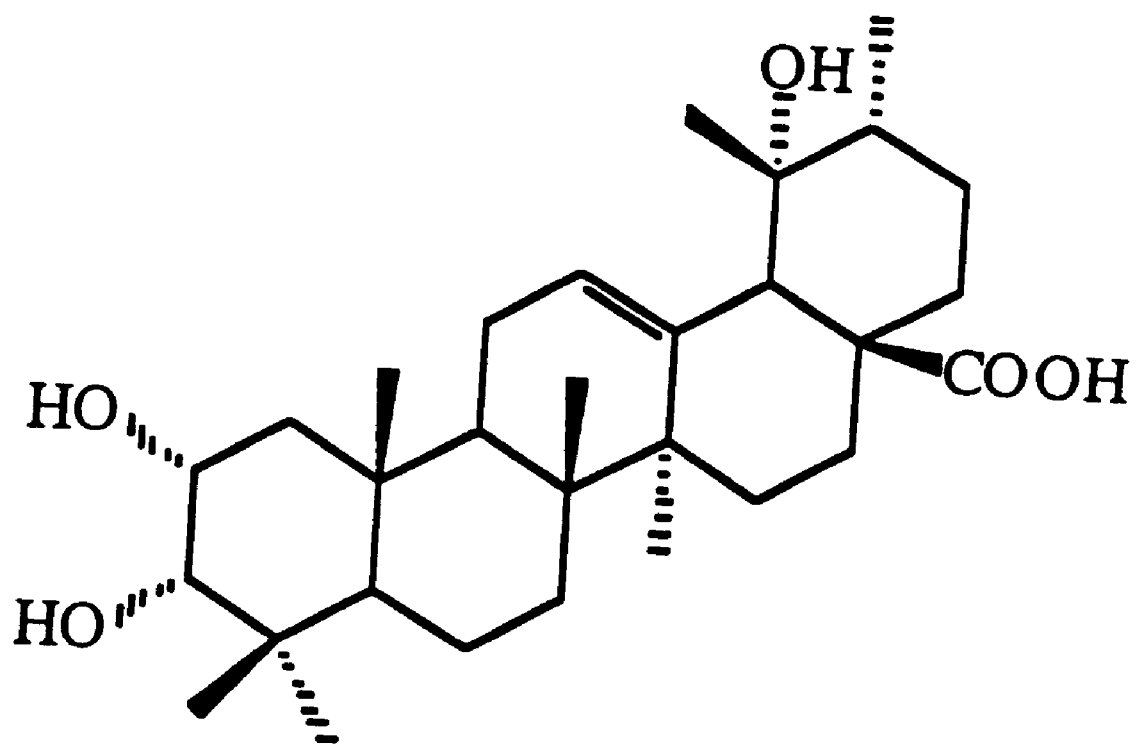
FIG. 5 shows the chemical formula of compound 5.
Figure 6:
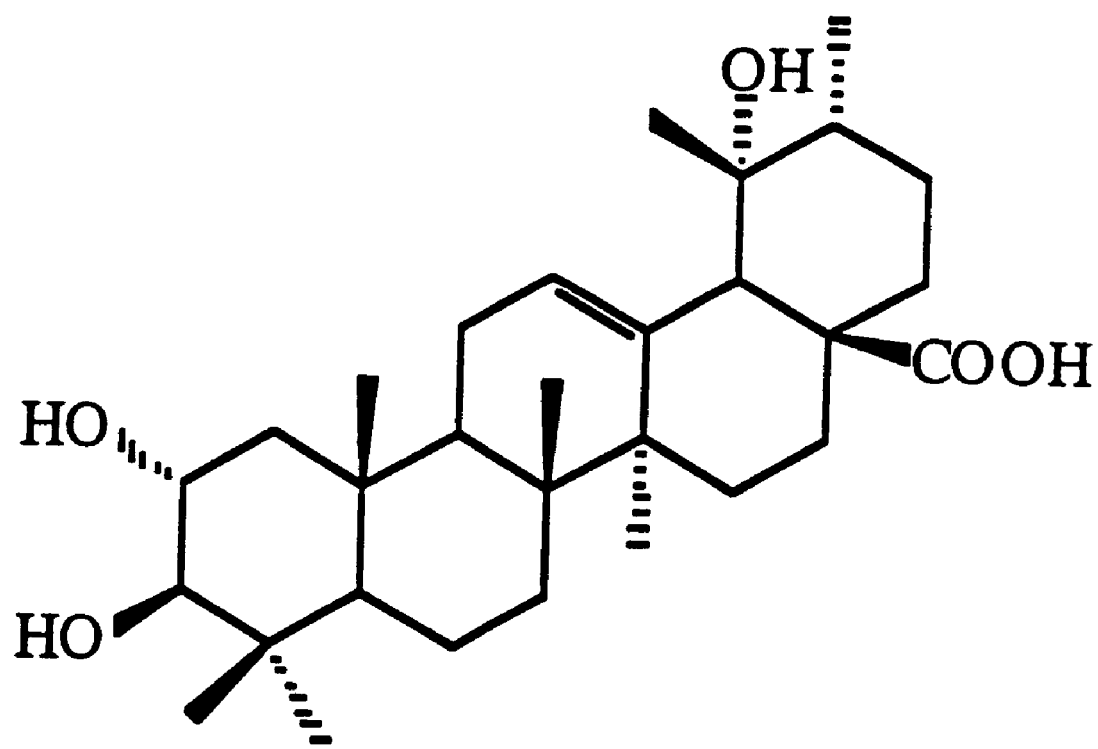
FIG. 6 shows the chemical formula of compound 6.

The $^{13}$C-NMR together with DEPT spectrum revealed thirty carbon signals including characteristic signals due to a trisubstituted double bond [$\delta$128.01 (d) and 139.96 (s)], a carboxylic acid group ($\delta$180.64) and two alcoholic carbons [$\delta$66.08 (d) and 79.34 (s)]. By direct comparison of data (NMR, IR, mp and MS) with those reported in the literature [29], compound 5 was identified to be 2,3,19-trihydroxy-12-ursen-28-oic acid or euscaphic acid as shown in FIG. 5.

6. 2,3,19-Trihydroxy-12-ursene-28-oic acid (6)

Compound 6 is a colourless powder with mp. 272–274° C. and $[\alpha]_D$−20 (pyridine, c 0.8). Its IR spectrum showed a hydroxyl group (3450 $cm^{-1}$) and carboxylic acid group (1690 $cm^{-1}$). Its mass spectrum showed m/z 488 $[M]^+$ and characteristic fragments at m/z 264, 219, 201, and 370 as compound 5. The difference between compound 6 and compound 5 was mainly in the $^{13}$C-NMR signals at C-2 (68.93 and 66.08 respectively) and C-3 (83.91 and 79.34 respectively). From the comparison of the $^{13}$C-NMR of 27 with tormentic acid [30, 31], the structure of compound 6 was deduced as 2,3,19-trihydroxy-12-ursene-28-oic acid or tormentic acid 7. 2,3,19,23-Tetrahydroxy-12-ursen-28-oic acid (7)

Figure 7:
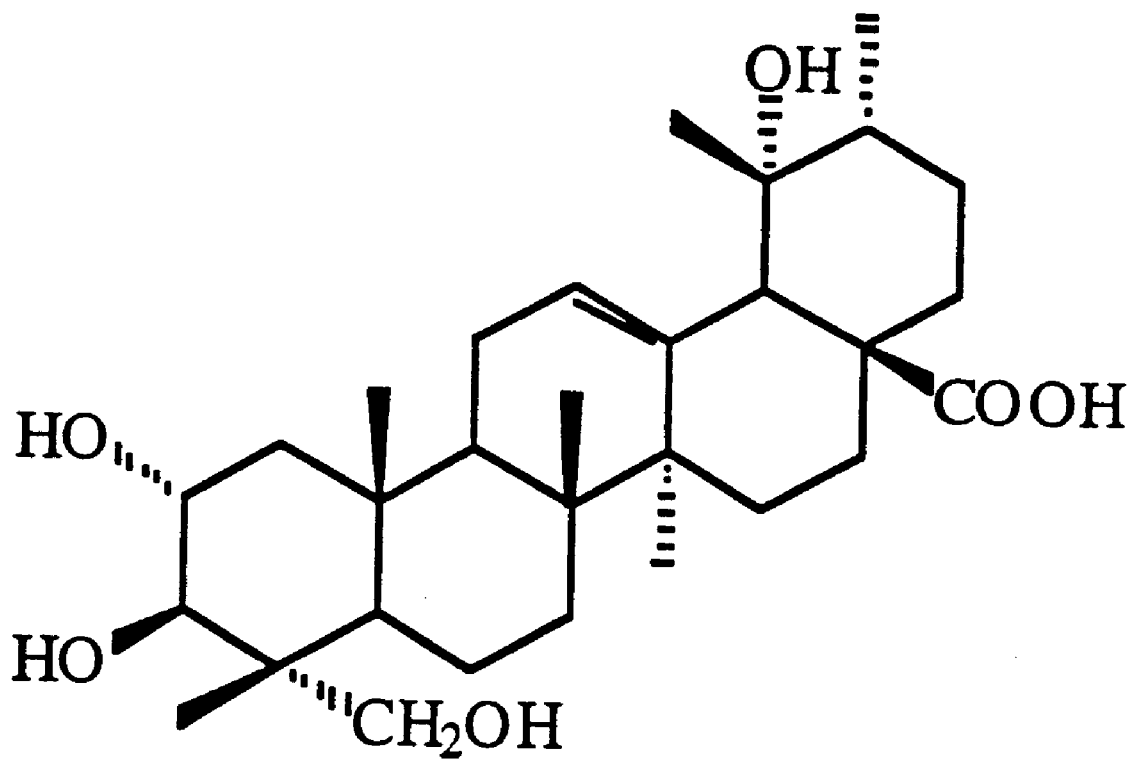
FIG. 7 shows the chemical formula of compound 7.

Compound 7 was obtained from fraction 3 with mp 301–304° C., $[\alpha]_D$+18.6. Its EI mass spectrum showed the molecular formula $C_{30}H_{48}O_6$ corresponding to the molecular weight 504 $[M]^+$. The characteristic fragmentations at m/z 264, 246, 219, 201, 146 are due to the retro-Diels-Alder cleavage of urs-12-en-28-oic acid derivatives bearing one free hydroxyl group in D or E ring [32]. The $^{13}$C-NMR spectrum of 7 was the same as that of 2,3,19,23-tetrahydroxy-12-ursene-28-oic acid [33]. The $^1$H-NMR spectrum of 7 showed six methyl groups including a secondary methyl group in ring E for 12-ursen skeleton, a hydroxy methylene at 3.71 (1H, d, J=10.2, 23-$H_a$) and 4.17 (1H, d, J=10.2, 23-$H_b$). By direct comparison of data (NMR, IR, mp and MS) with those reported in the literature [33,34], compound 7 was identified to be 2,3,19,23-tetrahydroxy-12-ursen-28-oic acid or 19-alphahydroxyasiatic acid as shown in FIG. 7.

8. 28-D-glucoside of 2,3,19-trihydroxy-12-ursen-28-oic-acid (8)

Figure 8:
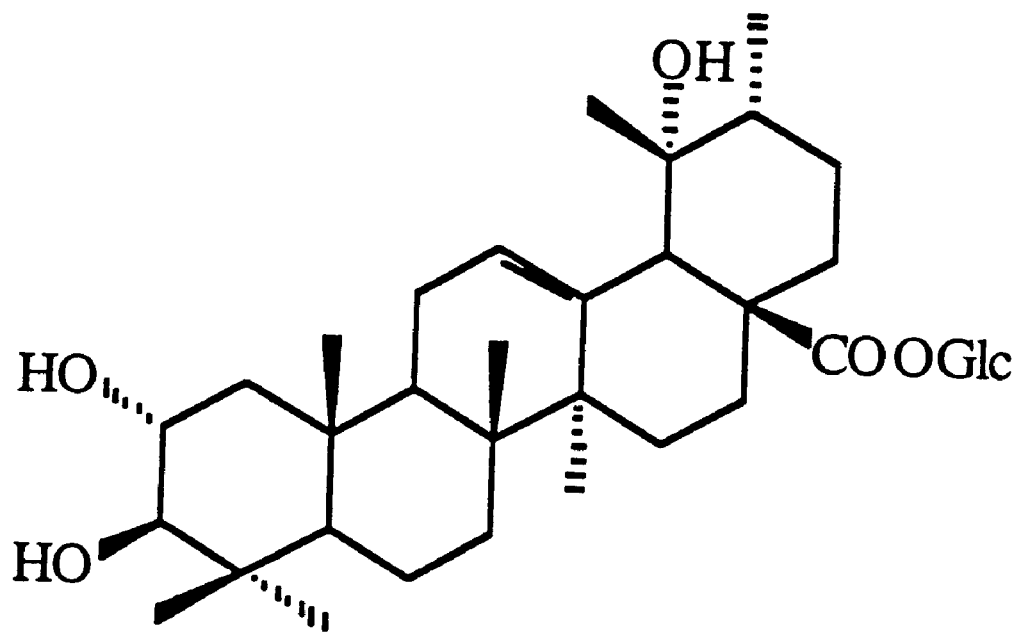
FIG. 8 shows the chemical formula of compound 8.

A series of conventional separations including repeated silica gel chromatography column and sephadex LH 20 chromatography column of fraction 5 yielded compounds 8–10. Compound 8 was obtained as colourless needles. The $^{13}$C-NMR spectrum of 8 showed a signal at 95.80 for an anomeric carbon confirming the presence of a sugar moiety, and a triterpene aglycone with an ursolic acid type skeleton [C-12 and C-13 at 128.35 (d) and 139.25 (s), respectively]. Its $^1$H-NMR spectrum also displayed signals at 6.26 (1H, d, J=8.1 Hz, 1'-H) for an anomeric proton and seven methyl groups including a secondary methyl group between 1.07 and 1.66 for the triterpene aglycone methyl protons. Basic hydrolysis of 8 provided glucose and 8, indicating that the glycosidation site on the aglycone is at the carboxyl function group. The identify of aglycone was confirmed as tormentic acid by comparison with an authentic sample as well as by cochromatography with compound 6. Thus, the structure of 8 is identified to be tormentic acid ester glucoside (28-D-glucoside of 2,3,19-trihydroxy-12-ursen-28-oic-acid) [35–36] as shown in FIG. 8.

9. 28-D-glucoside of 2,3,19α,23-tetrahydroxy-12-ursen-28-oic acid (9)

Figure 9:
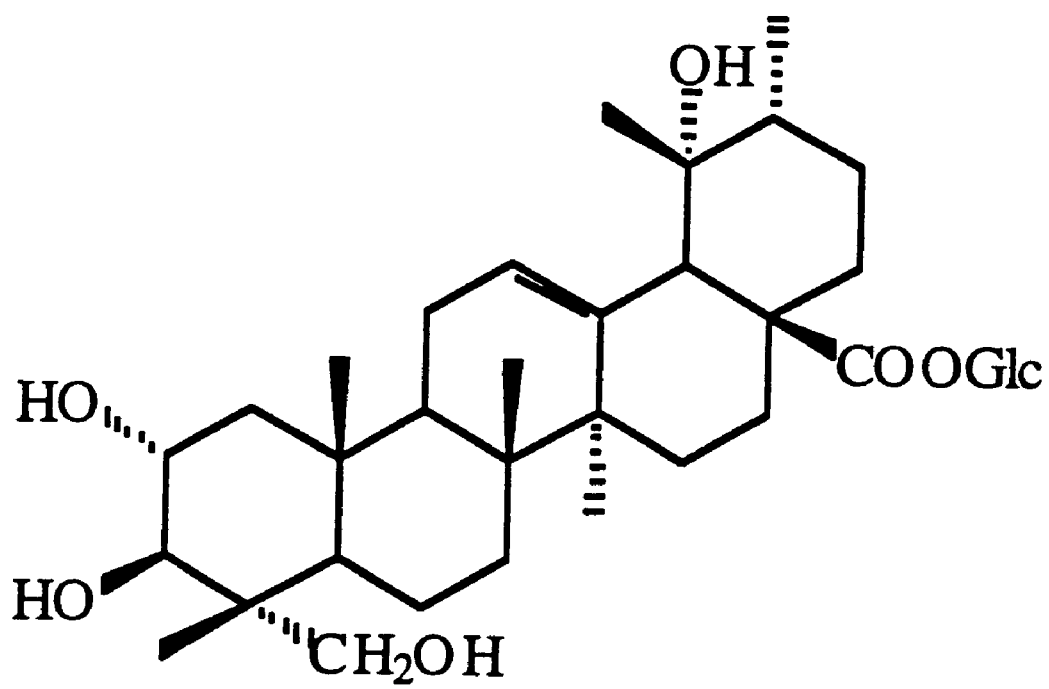
FIG. 9 shows the chemical formula of compound 9.

The $^{13}$C-NMR spectrum of 9 was quite similar to that of 8 with the only major difference arising from the appearance of a —$CH_2OH$ carbon signal at 66.66 in 9 and the absence of one of the signals corresponding to a methyl group in 8. Compound 9 underwent basic hydrolysis to yield glucose, indicating that the sugar is attached to the aglycone through ester linkage. The site of attachment for the —COOH group was established by comparison of the $^{13}$C-NMR spectral data of 9 with those reported in the literature for 23-hydroxyl tormentic acid glucoside [9]. The aglycone was identified to be asiatic acid by comparison with compound 7. Thus, compound 9 was identified as 23-hydroxyl-tormentic acid glucoside (28-D-glucoside of 2,3,19α,23-tetrahydroxy-12-ursen-28-oic acid) as shown in FIG. 9.

10. 3-D-glucopyranosyl sitosterol (10)

Figure 10:
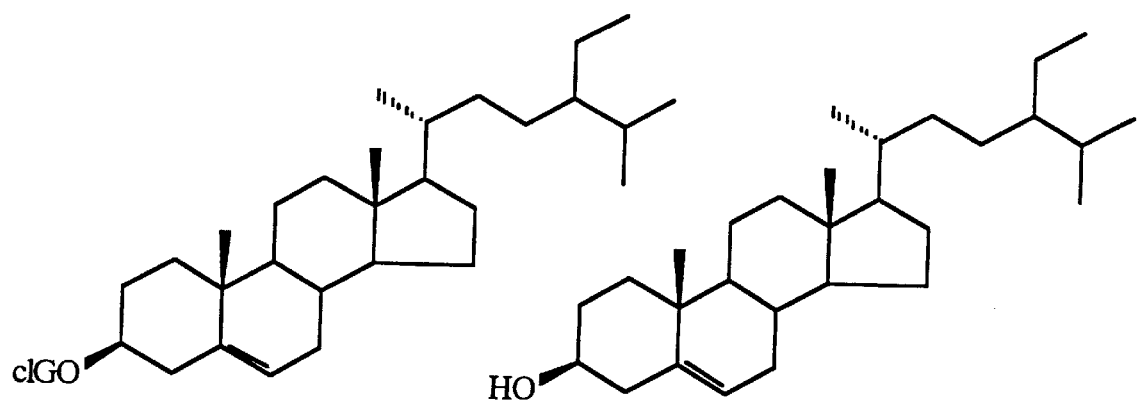
FIG. 10 shows the chemical formula of compounds 10 and 11.

The $^{13}$C-NMR spectrum of 10 showed a signal at 102.42 for an anomeric carbon confirming the presence of a sugar moiety, and a -sitosterol aglycone skeleton [C-5 and C-6 at 140.88 (s) and 121.85 (d) respectively]. The $^1$H-NMR spectrum also showed an anomeric proton at 4.94 (1H, d, J=7.7 Hz, 1'-H) and signals between 0.68 and 1.00 for six methyl group protons. Compound 10 was identified to be 3-D-glucopyranosyl sitosterol by comparison of data ($^{13}$C- and $^1$H-NMR data) with those reported in the literature [37–39] as shown in FIG. 10.

Compound 11 was identified to be β-sitosterol by comparison with an authentic sample.

Anti-HIV-1 Protease Activity Of The Isolated Compounds

Six of the compounds isolated from the EtOAc soluble fraction were tested for their anti-HIV-1 protease activity by HPLC assay [14]. As shown in Table 4, 2α,19α-dihydroxy-3-oxo-12-ursen-28-oic acid (1) (72%), ursolic acid (2) (85%) and maslinic acid (4) (100%) exhibited stronger activity than the others [epipomolic acid (3) (42%) and tormentic acid (6) (49%), respectively] at the concentration of 17.9 μg/ml. Maslinic acid (4) was the most active, while euscaphic acid (5) did not show activity at the tested concentration. This is the first report of anti-HIV-1 activity of this plant. The results of the experiments obtained in the present study indicate that compounds 1, 2 and 4 may contribute towards the anti-HIV-1 protease activity of the EtOAc soluble fraction of *G. japonicum*.

While the present invention has been described with reference to what are presently considered to be the preferred examples, it is to be understood that the invention is not limited to the disclosed examples. To the contrary, the invention is intended to cover various modifications and equivalent compounds included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Anti-HIV-1 protease activity of fractions from *G. japonicum*

| Fractions | Inhibiton(%) 0.0179 mg/ml |
|---|---|
| MeOH extract | 100.00 |
| Hexane soluble fraction | 4.86 |
| EtOAc soluble fraction | 100.00 |
| H$_2$O soluble fraction | 56.99 |

TABLE 2

$^{13}$C-NMR spectral data of compound 1 (δ relative to TMS in pyridine-d$_5$, 125 MHz)

| C | δ | C | δ | C | δ |
|---|---|---|---|---|---|
| 1 | 50.10 t | 11 | 24.12 t | 21 | 26.92 t |
| 2 | 69.73 d | 12 | 127.55 d | 22 | 38.45 t |
| 3 | 216.41 s | 13 | 140.07 s | 23 | 25.28 q |
| 4 | 48.10 s | 14 | 42.16 s | 24 | 21.77 q |
| 5 | 57.67 d | 15 | 29.26 t | 25 | 17.30 q |
| 6 | 19.55 t | 16 | 26.31 t | 26 | 16.77 q |
| 7 | 33.14 t | 17 | 48.25 s | 27 | 24.66 q |
| 8 | 40.37 s | 18 | 54.56 d | 28 | 180.65 s |
| 9 | 47.33 d | 19 | 72.67 s | 29 | 27.06 q |
| 10 | 37.90 s | 20 | 42.35 d | 30 | 15.95 q |

TABLE 3

$^1$H-$^{13}$C Long-range correlation detected in the HMBC spectrum of compound 1 (δ relative to TMS in pyridine-d$_5$)

| Proton[a] | Correlated C |
|---|---|
| 1.01 (H-24) | 216.41 (C-3), 48.10 (C-4), 57.67 (C-5) |
| 1.09 (H-26) | 33.14 (C-7), 40.37 (C-8), 47.33 (C-9), 42.16 (C-14) |
| 1.12 (H-30) | 72.67 (C-19), 26.92 (C-21) |
| 1.15 (H-25) | 50.10 (C-1), 57.67 (C-5), 47.33 (C-9) |
| 1.22 (H-23) | 216.41 (C-3), 48.10 (C-4), 57.67 (C-5) |
| 1.42 (H-29) | 54.56 (C-18), 72.67 (C-19), 42.35 (C-20) |
| 1.64 (H-27) | 40.37 (C-8), 140.07 (C-13), 42.16 (C-14), 29.26 (C-15) |
| 1.87 (H-9) | 50.10 (C-1), 40.37 (C-8), 37.90 (C-10), 17.30 (C-25), 16.77 (C-26) |
| 2.48 (H-1) | 69.73 (C-2), 216.41 (C-3), 37.90 (C-10), 17.30 (C-25) |
| 3.03 (H-18) | 127.55 (C-12), 140.07 (C-13), 42.16 (C-14), 26.31 (C-16), 48.25 (C-17), 72.67 (C-19), 42.35 (C-20), 180.65 (C-28) |
| 4.80 (H-2) | 50.10 (C-1) |
| 5.55 (H-12) | 47.33 (C-9), 42.16 (C-14), 54.56 (C-18) |

[a]δ in ppm.

TABLE 4

Inhibitory activity of compounds against HIV-1 protease using HPLC assay

| Compound | Inhibition (%) |
|---|---|
| 1 | 72.19 |
| 2 | 85.07 |
| 3 | 42.18 |
| 4 | 100.0 |
| 6 | 49.47 |

FULL CITATIONS FOR REFERENCES REFERRED TO IN THE SPECIFICATION

1. Ito, M. Nakashima, H., Baba M., Pauwels, R. Clereq. E. D., Shigeta, S., and Yamamoto, N., *Antiviral Res.*, 7, 127, 1987.
2. Wang., S. N., Milne, G. W. A., Yan, X. J., Posey, I. J., Nicklaus, M. C., Graham, L., and Rice, W. G., *J. Med. Chem.* 39, 2047, 1996.
3. Piacente, S., Pizza, C., Tommasi, N. D. and Mahmood, N., *J. Nat. Prod.*, 59, 565, 1996.
4. Hu, C. Q. Chen, K, Shi, Q. A. Kilkuskie, R. E. Cheng, Y. C., and Lee, K. H., *J. Nat. Prod.*, 52, 42, 1994.
5. Fujioka, T., Kashiwada, Y., Kilkuskie, R. E., Cosentino, I. M., Ballas, L. M., Jiang, J. B., Janzen, W. P., Chen, I. S., and Lee, K. H., *J. Nat. Prod.*, 57, 243, 1994.
6. Perry, L. M., in *Medicinal Plants of East and Southeast Asia*, MIT Press, Cambridge, Mass., pp. 343, 1980.
7. Yoshida, T., Maruyama, Y., Okuda, T, Memon, M. U., and Shingu, T., *Chem. Pharm. Bull.*, 30, 4245, 1982.
8. Yoshida, T., Maruyama, Y., Memon, M. U., Shingu, T., and Okuda, T, *Phytochemistry*, 24, 1041, 1985.
9. Shigenaga, S., Kouno, I., and Kawano, N., *Phytochemistry*, 24, 115, 1985.
10. Xu, H. X., Kadota, S., Wang, H., Kurokawa, M., Shiraki, K., Matsumoto, T., and Namba, T., *Heterocycles*, 38, 167, 1994.
11. Seelmeier, S., Schmidt, H., Turk, V., and Von der Helm, K. *Proc. Natl. Acad. Sci USA*, 85, 6612, 1988.
12. McQuade, T. J., Tomasselli, A. G., Liu, L, *Science*, 247, 454, 1990.
13. Ross, I. B., Martin, J. S., and David, P. F., *Biochem. Biophys. Res Commun.*, 188, 631, 1992.
14. Wan M. and Loh, B. N., *Biochem. Mol. International*, 35, 899, 1995.

15. Seo, S., Tomita, Y., and Tori, K., *Tetrahedron Lett.,* 17, 1975.
16. Kojima, H. and Ogura, H., *Phytochemistry,* 25, 729, 1986.
17. Kojima, H. and Ogura, H., *Phytochemistry,* 26, 1107, 1987.
18. Durham, D. G., Liu, X., and Richards, R. M. E., *Phytochemistry,* 36, 1469, 1994.
19. Yoshioka, I, Sugawara, T., and Kitagawa, I., *Chem. Pharm. Bull.,* 19, 1700, 1971.
20. Seto, T., Tanaka, O., and Naruhashi, N., *Phytochemistry,* 23, 2829, 1984.
21. Takahashi, K., Ogura, M., and Tanabe, Y., *Chem. Pharm. Bull.,* 17, 223, 1969.
22. Ogunkoya, L., *Phytochemistry,* 20, 121, 1981.
23. Seo, S., Tomita, Y., and Tori, K., *J. Am. Chem. Soc.,* 103, 2075, 1981.
24. Potier, P., Das, B. C., Bui, A., Janot, M., Pourrat, A., and Pourrat, H., *Bull Soc. Chim. Fr.,* 3458, 1986.
25. Romeo, G., Giannetto, P., and Aversa, M. C., *Org. Magn. Reson.,* 9, 29, 1977.
26. Bhacca, N. S. and Williams, D. H., in *Application of NMR Spectroscopy in Organic Chemistry,* Holden-Day, San Francisco, pp. 78, 1964.
27. Rogelio, P. M., and Mariano, G. F., *J. Nat. Pod.,* 51, 996, 1988.
28. Yagi, A., Okamura, N., Haraguchi, Y., Noda, K., and Nishioka, I., *Chem. Pharm. Bull.,* 26, 3075, 1978.
29. Takahashi, K., Kawaguchi, S., Nishimura, K. I., Kubota, K., Tanabe, Y., and Takani, M., *Chem. Pharm. Bull.,* 22, 650, 1974.
30. Villar, A., Paya, M., Hortiguela, M. D., and Cortes, D., *Planta Med.,* 52, 43, 1986.
31. Potier, P., Das, B. C., Bui, A. M., Janot, M. M., Pourrat, A., Pourrat, H., *Bull. Soc. Chim. Fr.,* 3458, 1966.
32. Bombardelli, E., Bonati, A., Gabetta, B., and Mustich, G., *Phytochemistry,* 13, 2559, 1974.
33. Higuchi, R., Kawasaki, T., Biswas, N., Pandey, V. B., and Dasgupta, B., *Phytochemistry,* 21, 907, 1982.
34. Polonsky, J., *Bull. Soc. Chim. Fr.,* 173, 1953.
35. Gopalsamy, N., Vargas, D., Gueho, J., Ricaud, C., and Hostettmann, K., *Phytochemistry,* 27, 3593, 1988.
36. Du, H. Q., Zhao, X., Zhao, T. Z., Wang, M. T., Zhang, Z. W., Yao, M., and Yu, S. Z., *Yaoxue Xuebuo,* 18, 314, 1983.
37. Misra, A. N. and Tiwari, H. P., *Phytochemistry,* 12, 393, 1973.
38. Dzizenko, A. K., Isakov, V. V., Uvarova, N. I., Oshitok, G. I., and Elyakov, G. B., *Carbohyd. Res.,* 27, 249, 1973.
39. Iribarren, A. M. and Pomilio, A. B., *J. Nat. Prod.,* 46, 752, 1983.

We claim:

1. A composition for treating a retroviral infection comprising 2-alpha, 19-alpha-dihydroxy-3-oxo-12-ursen-28-oic acid; and pharmaceutically acceptable salts thereof in admixture with a physiologically acceptable diluent or carrier.

2. A method of treating a retroviral infection comprising administering a therapeutically effective amount of a triterpene selected from the group consisting of 2-alpha, 19-alpha-dihydroxy-3-oxo-12-ursen-28-oic acid and maslinic acid and pharmaceutically acceptable salts thereof to a mammal in need of such a treatment.

3. A method according to claim 2 wherein said triterpene is 2-alpha, 19-alpha-dihydroxy-3-oxo-12-ursen-28-oic acid.

4. A method according to claim 2 wherein said retroviral infection is Human Immunodeficiency Virus (HIV).

5. A method according to claim 2 wherein said triterpene is maslinic acid.

6. A compound 2-alpha, 19-alpha-dihydroxy-3-oxo-12-ursen-28-oic acid.

* * * * *